Figure 1A:
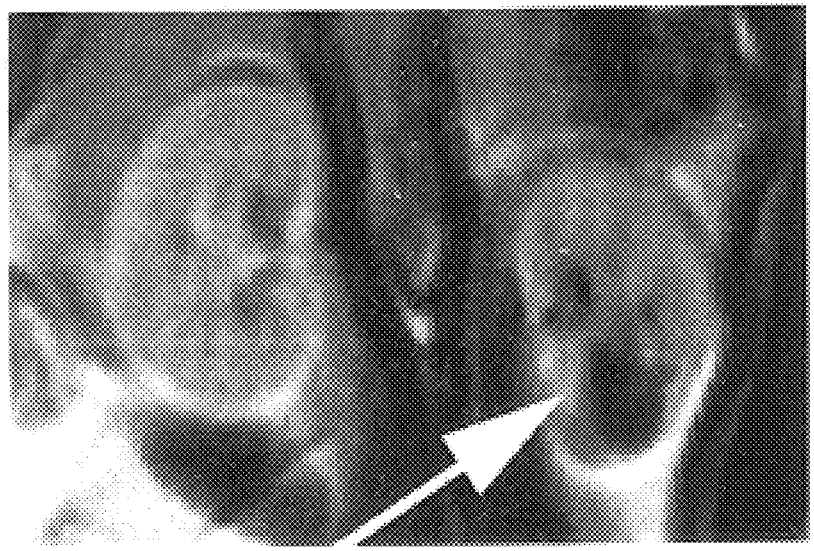

United States Patent [19]
Platzek et al.

[11] Patent Number: 6,083,479
[45] Date of Patent: Jul. 4, 2000

[54] CONTRAST MEDIA FOR INFARCTION AND NECROSIS IMAGING

[75] Inventors: Johannes Platzek; Ulrich Niedballa; Bernd Raduechel, all of Berlin; Wolfgang Ebert, Mahlow; Hanns Joachim Weinmann, Berlin, all of Germany

[73] Assignee: Schering Aktiengesellschaft, Germany

[21] Appl. No.: 09/157,959

[22] Filed: Sep. 22, 1998

[30]   Foreign Application Priority Data

Sep. 26, 1997 [DE] Germany .................... 197 44 003

[51] Int. Cl.⁷ .................... A61B 5/055; A61K 49/04
[52] U.S. Cl. .................... 424/1.65; 424/9.363; 424/9.42; 534/16; 540/465; 540/474; 514/184; 514/836
[58] Field of Search .................... 424/9.363, 9.362, 424/1.65, 9.42; 540/465, 471, 474; 534/16; 514/184, 836; 436/173; 600/420

[56]   References Cited

U.S. PATENT DOCUMENTS

| | | |
|---|---|---|
| 5,277,895 | 1/1994 | Platzek et al. .................... 424/9 |
| 5,364,614 | 11/1994 | Platzek et al. .................... 424/9.3 |
| 5,446,145 | 8/1995 | Love et al. .................... 540/465 |
| 5,650,133 | 7/1997 | Carvalho et al. .................... 424/1.65 |
| 5,681,544 | 10/1997 | Schmitt-Willich et al. ........... 424/9.34 |
| 5,756,065 | 5/1998 | Wilson et al. .................... 424/1.53 |
| 5,874,061 | 2/1999 | Schmitt-Willich et al. ......... 424/9.363 |
| 5,911,971 | 6/1999 | Platzek et al. .................... 424/9.363 |
| 5,958,373 | 9/1999 | Garrity et al. .................... 424/1.65 |
| 5,972,307 | 10/1999 | Carvalho et al. .................... 424/1.65 |

*Primary Examiner*—Gary E. Hollinden
*Attorney, Agent, or Firm*—Millen, White, Zelano & Branigan, P.C.

[57]   ABSTRACT

The invention relates to new compounds that are suitable as contrast media especially for infarction and necrosis imaging, process for their production and pharmaceutical agents that contain these compounds.

19 Claims, 3 Drawing Sheets

CONTRAST MEDIA FOR INFARCTION AND NECROSIS IMAGING

The invention relates to the subject that is characterized in the claims, namely new compounds that are suitable as contrast media especially for infarction and necrosis imaging, process for their production and pharmaceutical agents that contain these compounds.

Detection, localization and monitoring of necroses or infarctions is an important area in medicine. Myocardial infarction is not a stationary process, but rather a dynamic process that extends over a prolonged period (weeks to months). The disease proceeds in about three phases, which overlap rather than being distinctly separated from one another. The first phase, the development of myocardial infarction, comprises the 24 hours after the infarction, in which the destruction progresses like a shock wave (wave front phenomenon) from the subendocardium to the myocardium. The second phase, the already existing infarction, comprises the stabilization of the area in which the formation of fibers (fibrosis) takes place as a healing process. The third phase, the healed infarction, begins after all destroyed tissue is replaced by fibrous scar tissue. During this period, extensive restructuring takes place.

Up until now, no precise and reliable process has been known that would make it possible to diagnose the current phase of a myocardial infarction in a living patient. For evaluating a myocardial infarction, it is of decisive importance to know the extent of the portion of tissue that is definitively lost in the infarction and at what point the loss took place since the type of treatment depends on this information.

Infarctions occur not only in the myocardium but also in other tissues, especially in the brain.

While infarction can be healed to a certain extent, in the case of necrosis, locally limited tissue death, only the harmful sequelae for the rest of the organism can be prevented or at least mitigated. Necroses can develop in many ways: due to injuries, chemicals, oxygen deficits or by radiation. As with infarction, knowing the extent and nature of a necrosis is important for further medical treatment.

Attempts were therefore made even early on to improve the localization of infarctions and necroses by using contrast media in noninvasive processes such as scintigraphy or nuclear spin tomography. The literature devotes a great deal of space to attempts to use porphyrins for necrosis imaging. The results that are achieved, however, paint a contradictory picture. Thus, Winkelman and Hoyes described in Nature, 200, 903 (1967) that manganese-5,10,15,20-tetrakis(4-sulfonatophenyl)-porphyrin (TPPS) accumulates in a selective manner in the necrotic portion of a tumor.

Lyon et al. (Magn. Res. Med. 4, 24 (1987)), however, observed that manganese-TPPS is dispersed in the body, specifically in the kidneys, liver, tumor and only to a small extent in the muscles. In this case, it is advantageous that the concentration in the tumor reaches its maximum only on the 4th day and also did so only after the authors had increased the dose from 0.12 mmol/kg to 0.2 mmol/kg. The authors therefore also speak of a non-specific uptake of TPPS in the tumor. Bockhurst et al. again report in Acta Neurochir 60, 347 (1994, Suppl.) that MnTPPS bonds to tumor cells in a selective manner.

In turn, Foster et al. (J. Nucl. Med. 26, 756 (1985)) found that [111]In-5,10,15,20-tetrakis-(4-N-methyl-pyridinium)-porphyrin (TMPyP) does not accumulate in the necrotic portion, but rather in the living marginal layers. It can be concluded from the above that a porphyrin-tissue interaction exists, is obvious, but is not compelling.

In Circulation Vol. 90, No. 4, Part 2, page 1468, Abstract No. 2512 (1994), Ni et al. report that they can visualize infarction areas with a manganese-tetraphenyl-porphyrin (Mn-TPP) and a gadolinium-mesoporphyrin (Gd-MP). In International Patent Application WO 95/31219, both substances were used in infarction and necrosis imaging. The authors Marchal and Ni write (see Example 3) that for the compound Gd-MP, the metal content of the infarction kidneys was just as high as that of the non-infarcted organ, but that it was nine times as high for the myocardium in infarcted tissue (Example 1). It was surprising that the ratio of the signal intensities in MRI for infarcted tissue in comparison with healthy tissue was comparatively high at 2.10 or 2.19 in both cases.

Porphyrins tend to be deposited in the skin, which leads to photosensitization. The sensitization can take days or even weeks. This is an undesirable side effect when porphyrins are used as diagnostic agents. In addition, the therapeutic index for porphyrins is very low since, e.g., Mn-TPPS uses an action only at a dose of 0.2 mmol/kg, but the $LD_{50}$ is already approximately 0.5 mmol/kg.

To date, there are thus no compounds that can be used satisfactorily as contrast media in infarction and necrosis imaging. The object of this invention was therefore to synthesize new compounds that satisfy the requirements of a diagnostic agent for this special purpose and overcome the drawbacks of compounds that are known to date.

This object is achieved with the compounds of general formula I:

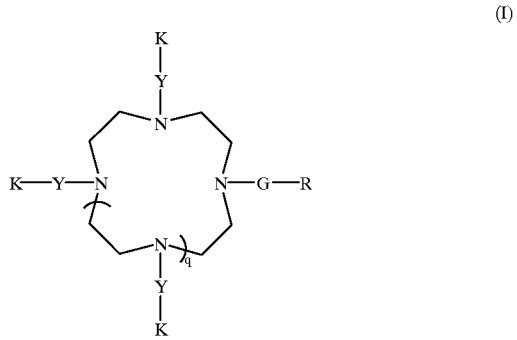

(I)

in which q means a number 1, 2 or 3,

G is a direct bond, an $SO_2$ or a CO group,

K stands for a metal complex or its salts of organic and/or inorganic bases or amino acids or amino acid amides, R is an unbranched or branched $C_4$–$C_{30}$ hydrocarbon chain, which optionally is substituted by 1–2 amino groups, 1–5 OH groups, 1–5 $OR^1$ groups with $R^1$ meaning a $C_1$–$C_6$ alkyl group, 1 NH-K group, 1–3 carboxy groups, 1–2 aliphatic or 1–3 aromatic rings, and which optionally contains 1–6 amide groups, 1–2 $SO_2$ groups, 1–2 sulfur atoms, 1–6 oxygen atoms, 1–2 aliphatic or 1–3 aromatic rings, whereby the aromatic rings are optionally substituted with 1–2 chlorine atoms, 1–2 acid groups, 1–2 $OR^1$ groups or 1–2 $C_1$–$C_6$ alkyl groups, Y is a direct bond or a chain of general formula II or III:

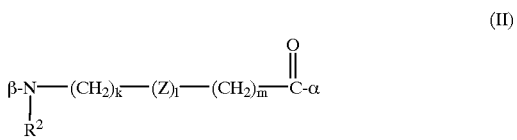

(II)

-continued

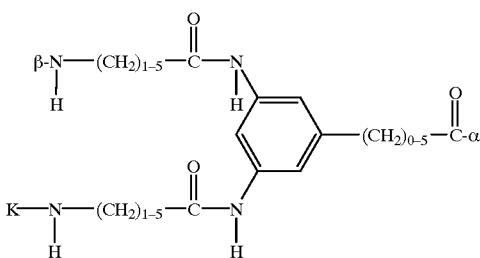 (III)

in which

R² is a hydrogen atom, a phenyl group, a benzyl group or a $C_1$–$C_7$ alkyl group, which optionally is substituted with a carboxy group, a methoxy group or a hydroxy group, Z is a polyglycol ether group with up to 5 glycol units or a molecule portion of general formula IV $$—CH(R^3)— \quad (IV),$$

in which R³ is a $C_1$–$C_{10}$ alkyl radical, a carboxylic acid with 1–7 carbon atoms, a phenyl group, a benzyl group or a —$(CH_2)_{1-5}$—NH-K group, α indicates the bond to the nitrogen atom of the skeleton chain, β indicates the bond to metal complex K, and in which variables k and m stand for natural numbers between 0 and 10 and 1 stands for 0 or 1.

The new compounds have several basic advantages compared to the known compounds. They have a high relaxivity in the NMR experiment, which has the result that the compounds can be administered in small doses for nuclear spin tomographic studies. They are especially suitable for necrosis imaging, which is shown by the pharmacological examples below. The compounds according to the invention are very well tolerated and are excreted completely. In contrast to the porphyrins, they are not deposited in the skin and do not produce any photosensitization. For use of the compounds according to the invention in diagnostic radiology, it is necessary to administer higher doses. Owing to the good compatibility of the compounds, however, this constitutes no obstacle for use in diagnostic radiology.

Among the new compounds of general formula I according to the invention, those with q meaning number 1 are preferred.

In general formula II, R² in the meaning of a hydrogen atom is preferred.

In general formula IV, R³ in the meaning of a carboxylic acid with 1 to 4 carbon atoms or a —$(CH_2)_{1-5}$—NH-K group is preferred.

As molecule portion Y, the following structures can be mentioned by way of example:

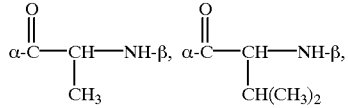

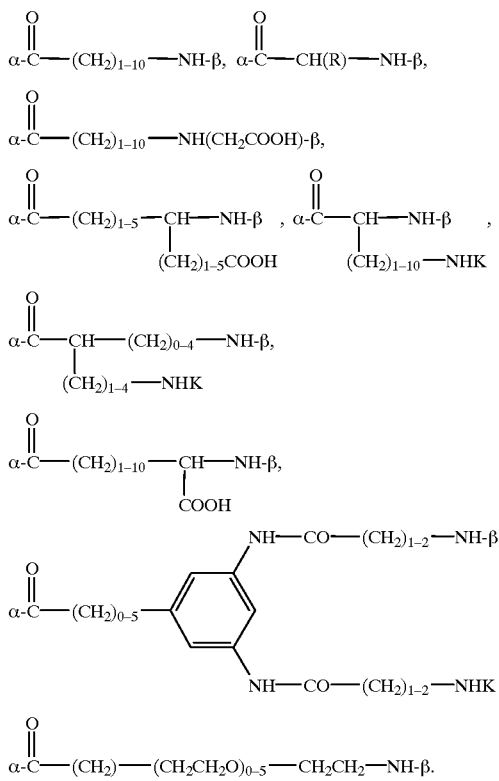

Preferred molecule portions Y are the direct bond as well as the following structures:

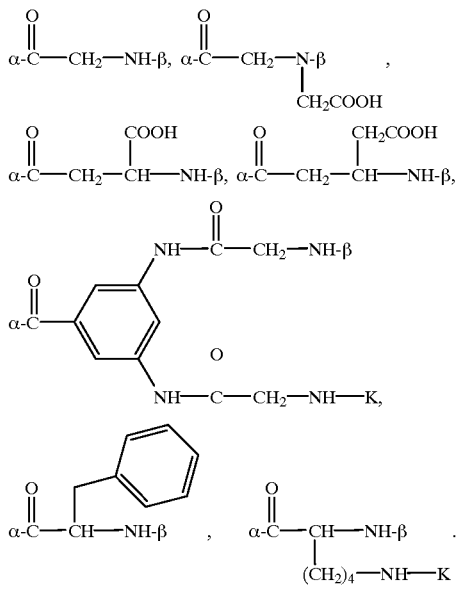

The complexing agents or metal complexes have the following structures:

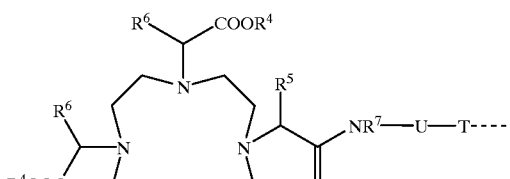 (V)

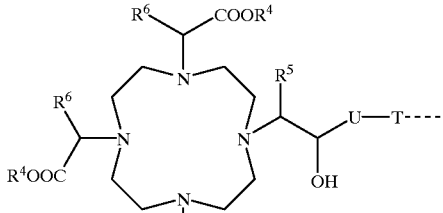 (VI)

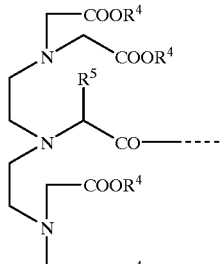 (VII)

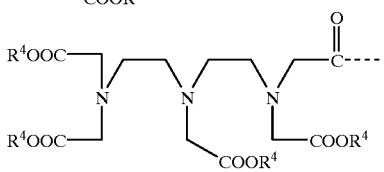 (VIII)

whereby

R⁴, independently of one another, are a hydrogen atom or a metal ion equivalent of the elements of atomic numbers 20–32, 37–39, 42–44, 49 or 57–83, provided that at least two of substituents R⁴ stand for a metal ion equivalent of the above-mentioned elements, R⁵ is a hydrogen atom or a straight-chain, branched, saturated or unsaturated $C_1$–$C_{30}$ alkyl chain, which optionally is substituted by 1–5 hydroxy, 1–3 carboxy or 1 phenyl group(s) and/or optionally is interrupted by 1–10 oxygen atoms, 1 phenylene or 1 phenylenoxy group, R⁶ is a hydrogen atom, a straight-chain or branched $C_1$–$C_7$ alkyl radical, a phenyl or benzyl radical, R⁷ is a hydrogen atom, a methyl or ethyl group, which optionally is substituted by a hydroxy or carboxy group, U is a straight-chain, branched, saturated or unsaturated $C_1$–$C_{20}$ hydrocarbon chain that optionally contains 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups, 1–10 oxygen, 1–5 sulfur and/or 1–5 nitrogen atoms and/or optionally is substituted by 1–5 hydroxy, 1–2 mercapto, 1–5 oxo, 1–5 thioxo, 1–3 carboxy, 1–5 carboxyalkyl, 1–5 ester and/or 1–3 amino groups, whereby the optionally contained phenylene groups can be substituted by 1–2 carboxy, 1–2 sulfone or 1–2 hydroxy groups, T stands for a —CO—β, —NHCO—β or —NHCS—βgroup, whereby β indicates the binding site to Y.

Substituent R⁵ is preferably a hydrogen atom, a $C_1$–$C_7$ chain or a phenyl or benzyl group, which optionally is substituted by a hydroxymethyl group or 1–2 OH groups.

As especially preferred substituents R⁵, there can be mentioned:

the hydrogen atom, the methyl, ethyl, propyl, isopropyl, benzyl, phenyl group,
—CH₂CH₂OH,
—CH₂OH, —CH₂—COOH, —COOH,
—CH₂CHOHCH₂OH, —CH₂O—CH₂CH₂OCH₃,
—CH₂OCH₃, —CH₂—O—C₆H₄—COOH.

As preferred substituents R⁶, there can be mentioned:

the hydrogen atom, the methyl, ethyl, propyl, isopropyl, benzyl and phenyl group, whereby the hydrogen atom is especially preferred.

As preferred substituents R⁷, there can be mentioned:

the hydrogen atom, the methyl, ethyl, —CH₂CH₂OH, —CH₂—COOH group, whereby the hydrogen atom is especially preferred.

The $C_1$–$C_{20}$ hydrocarbon chain that stands for U and that is preferably a $C_1$–$C_{10}$ hydrocarbon chain preferably contains the following groups:
—CH₂NHCO—, —NHCOCH₂O—,
—NHCOCH₂OC₆H₄—, —N(CH₂CO₂H)—,
—CH₂OCH₂—,
—NHCOCH₂C₆H₄—, —NHCSNHC₆H₄—,
—CH₂OC₆H₄—, —CH₂CH₂O— and/or is substituted by groups —COOH and —CH₂COOH.

As examples of U, the following groups are cited:
CH₂—, —CH₂CH₂—, —CH₂CH₂CH₂—, —C₆H₄—,
—C₆H₁₀—, —CH₂C₆H₄—,
—CH₂NHCOCH₂CH (CH₂CO₂H)—C₆H₄—,
—CH₂NHCOCH₂OCH₂—,
—CH₂NHCOCH₂C₆H₄—,

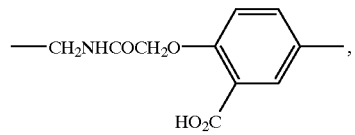

—CH₂NHCSNH—C₆H₄—CH (CH₂COOH) CH₂—,
—CH₂OC₆H₄—N(CH₂COOH) CH₂—,
—CH₂NHCOCH₂O(CH₂CH₂O )₄—C₆H₄—,
—CH₂O—C₆H₄—,
—CH₂CH₂—O—CH₂CH₂—, —CH₂CH₂—O—CH₂CH₂—O—CH₂CH₂—,

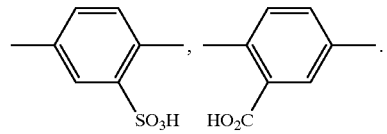

In this case, especially preferred are the following groups:
—CH₂—, —CH₂CH₂—, —CH₂CH₂CH₂—, —C₆H₄—,
—C₆H₁₀—, —CH₂C₆H₄—,
—CH₂NHCOCH₂CH(CH₂CO₂H)—C₆H₄—,
—CH₂NHCOCH₂OCH₂—,
—CH₂NHCOCH₂C₆H₄—,
—CH₂NHCSNH—C₆H₄—CH(CH₂COOH) CH₂—,
—CH₂OC₆H₄-N(CH₂COOH)CH₂—,
—CH₂NHCOCH₂O(CH₂CH₂O)₄—C₆H₄—,
—CH₂O—C₆H₄—,

—CH$_2$CH$_2$—O—CH$_2$CH$_2$—, —CH$_2$CH$_2$—O—CH$_2$CH$_2$—O—CH$_2$CH$_2$—.

As examples of K, the following structures can be cited:

an O—C$_n$H$_{2n+1}$ group, an O—(CH$_2$)$_n$—COOH group, an —O—(CH$_2$CH$_2$)$_r$—C$_n$H$_{2n+1}$ group or an NH—CO—C$_n$H$_{2n+1}$ group, with n=1–15 and r=1–5.

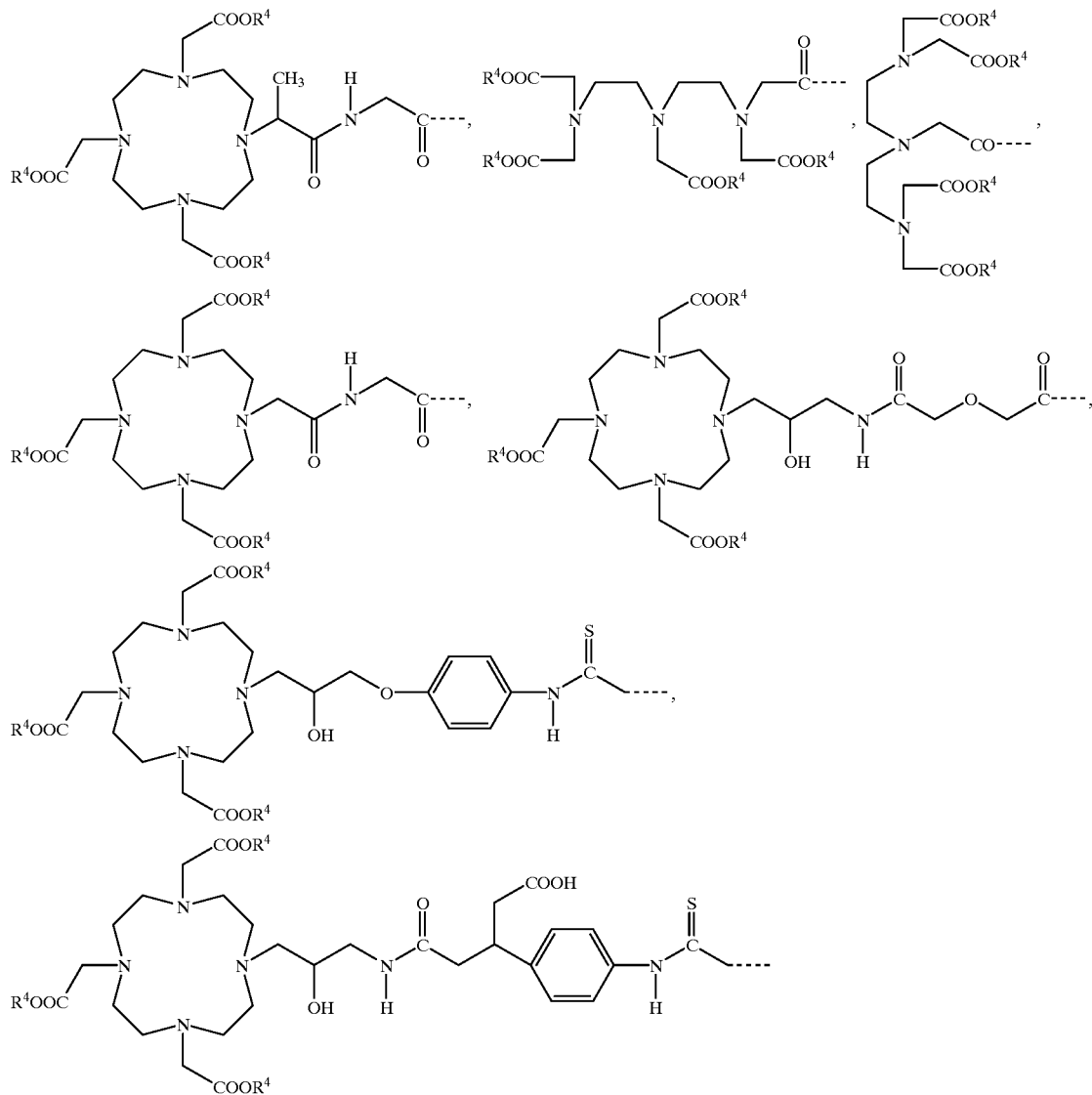

whereby the first five mentioned above are preferred.

As molecule portion G, the direct bond or the CO group is preferred.

Molecule portion R can be a group of general formula IX:

(IX)

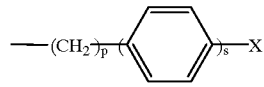

in which p stands for numbers 0 to 25 and s stands for 0, 1 or 2, and p and s are not zero at the same time, and in which X is a hydrogen atom, a methyl group, a carboxyl group, an OH group, an OCH$_3$ group, a CONH$_2$ group, a chlorine atom, a C$_1$–C$_{10}$ alkyl chain, In addition, R can be one of the following groups:

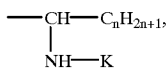

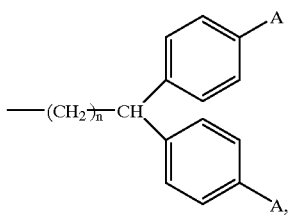

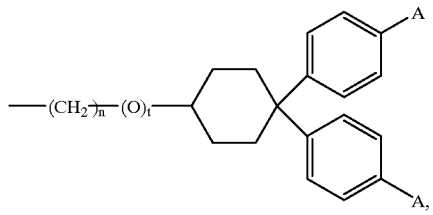

in which n=1–15, t=0 or 1, and A means a hydrogen atom, a chlorine atom or an OCH₃ group.

Preferred are compounds in which G and R together have one of the following structure:

—CO—C₁₅H₃₁, —CO—C₁₄H₂₉, —CO—C₁₃H₂₇, —CO—C₁₀H₂₀—NH—CO—C₆H₁₃,
—CO—C₆H₁₃, —CO—CH₂—O—CH₂CH₂—O—C₁₀H₂₁, —CO—CH₂—O—C₁₃H₂₇, —C₁₅H₃₁,
—C₁₄H₂₉, —SO₂—C₁₃H₂₇, —SO₂—C₁₄H₂₉, —SO₂—C₁₅H₃₁,

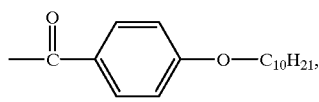

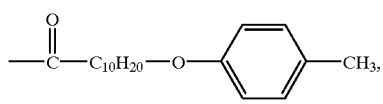

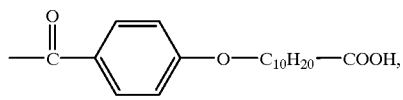

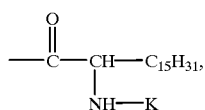

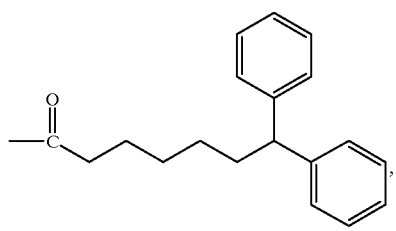

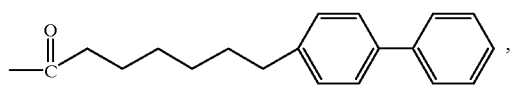

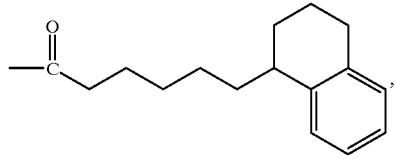

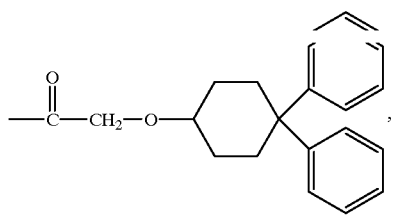

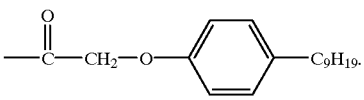

If the agent according to the invention is intended for use in NMR diagnosis, the central ion of the complex salt must be paramagnetic. These are especially the divalent and trivalent ions of the elements of atomic numbers 21–29, 42, 44 and 58–70. Suitable ions are, for example, the chromium (III), iron(II), cobalt(II), nickel(II), copper(II), praseodymium(III), neodymium(III), samarium(III) and ytterbium(III) ion. Because of their very strong magnetic moment, the gadolinium(III), terbium(III), dysprosium(III), holmium(III), erbium(III), manganese(II) and iron(III) ions are especially preferred.

For use of the compounds according to the invention in nuclear medicine, the metal ion must be radioactive. Suitable are, for example, radioisotopes of the elements copper, cobalt, gallium, germanium, yttrium, strontium, technetium, indium, ytterbium, gadolinium, samarium, iridium, rhenium and bismuth; preferred are technetium, gallium, indium and rhenium.

If the agent according to the invention is intended for use in diagnostic radiology, the central ion must be derived from an element of a higher atomic number to achieve a sufficient absorption of x rays. It has been found that for this purpose, diagnostic agents, which contain a physiologically compatible complex salt with central ions of elements of atomic numbers between 21–29, 39, 42, 44, 57–83, preferably 25, 26 and 57–83, are suitable; these are, for example, the lanthanum(III) ion and the above-mentioned ions of the lanthanide series.

In this case, especially preferred are manganese(II), iron (II), iron(III), praseodymium(III), neodymium(III), samarium(III), gadolinium(III), ytterbium(III) or bismuth (III) ions and especially dysprosium(III) ions.

The residual acid hydrogen atoms, i.e., those that have not been substituted by the central ion, can be replaced optionally completely or partially by cations of inorganic and/or organic bases, amino acids or amino acid amides.

Suitable inorganic cations are, for example, the lithium ion, the potassium ion, the calcium ion, the magnesium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and ornithine as well as the amides of otherwise acidic or neutral amino acids.

The production of the compounds of general formula I according to the invention is carried out in that compounds of general formula I'

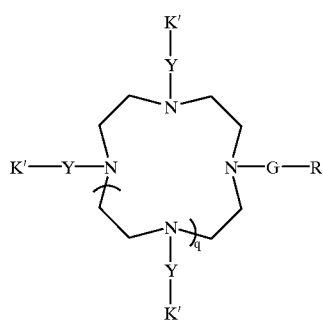
(I')

in which K' stands for K, with R⁴ meaning a hydrogen atom or a carboxy protective group, are reacted, after the optionally present protective groups are cleaved off, in a way known in the art, with at least one metal oxide or metal salt of an element of atomic numbers 20–32, 37–39, 42–44, 49 or 57–83 and optionally then still present acid hydrogen atoms are substituted completely or partially by cations of inorganic and/or organic bases, amino acids or amino acid amides in the complex compounds that are thus obtained.

If K stands for a tetraazamacrocycle, the synthesis of the compounds according to the invention also is carried out in such a way that a compound of general formula I"

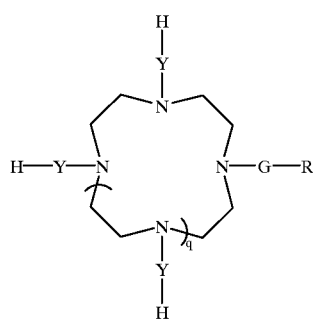
(I")

is reacted with a complex V' or VI',

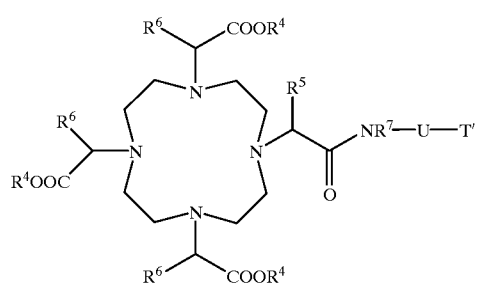
(V')

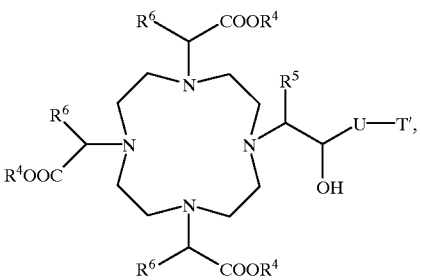
(VI')

whereby T' stands for a —C*O, —COOH, —N=C=O or —N=C=S group and —C*O stands for an activated carboxyl group, and radicals R⁴ to R⁷ are defined as above, provided that optionally other carboxyl groups are present in the form of their salts with inorganic and/or organic bases, amino acids or amino acid amides.

As examples of an activated carbonyl group C*O. anhydride, p-nitropheny lester, N-hydroxysuccinimide ester, pentaf luorophenyl ester and acid chloride can be mentioned.

If R⁴ stands for an acid protective group, lower alkyl, aryl and aralkyl groups, for example, the methyl, ethyl, propyl, butyl, phenyl, benzyl, diphenylmethyl, triphenylmethyl, bis-(p-nitrophenyl)-methyl group, as well as trialkylsilyl groups are suitable.

The optionally desired cleavage of the protective groups is carried out according to the processes that are known to one skilled in the art (see, e.g., E. Wünsch, Methoden der Org. Chemie [Methods of Organic Chemistry], Houben-Weyl, Volume XV/1, 4th Edition 1974, p. 315), for example, by hydrolysis, hydrogenolysis, alkaline saponification of the ester in aqueous-alcoholic solution at temperatures of 0° C. to 50° C., acid saponification with mineral acids or in the case of tert-butylesters with the aid of trifluoroacetic acid.

The introduction of the desired metal ions is carried out as was disclosed in, e.g., German laid-open specification 34 01 052, by the metal oxide or a metal salt (for example, the nitrate, acetate, carbonate, chloride or sulfate) of the element of atomic numbers 20–32, 37–39, 42–44, 57–83 being dissolved or suspended in water and/or a lower alcohol (such as methanol, ethanol or isopropanol) and being reacted with the solution or suspension of the equivalent amount of the complexing ligand and then, if desired, existing acid hydrogen atoms of the acid groups being substituted by cations of inorganic and/or organic bases, amino acids or amino acid amides.

The introduction of the desired metal ions can be done both in the stage of general formula I' or before the coupling of structural parts K, i.e., in the stage of the production of complexes V' or VI'.

In this case, neutralization is carried out with the aid of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methyl- and N,N-dimethylglucamine, as well as basic amino acids, such as, for example, lysine, arginine and ornithine or of amides of originally neutral or acidic amino acids, such as, for example, glycinamide.

For the production of neutral complex compounds, enough of the desired bases can be added to, for example, the acidic complex salts in aqueous solution or suspension to ensure that the neutral point is reached. The solution that is obtained can then be evaporated to the dry state in a vacuum. Often, it is advantageous to precipitate the neutral salts that are formed by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and to obtain crystallizates that are easily isolated and readily purified. It has proven especially advantageous to add the desired base as early as during the complexing of the reaction mixture and thus to save a process step.

If the acidic complex compounds contain several free acid groups, it is often suitable to produce neutral mixed salts that contain both inorganic and organic cations as counterions.

This can be done by, for example, the complexing ligands in aqueous suspension or solution being reacted with the oxide or salt of the element that provides the central ion and half of the amount of an organic base that is required for neutralization, the complex salt formed being isolated, optionally purified and then mixed with the required amount of inorganic base for complete neutralization. The sequence of adding a base can also be reversed.

The purification of the complexes that are thus obtained is carried out optionally after the pH is adjusted by adding an acid or base to pH 6 to 8, preferably about 7, preferably by ultrafiltration with membranes of suitable pore size (e.g., Amicon®YM1, Amicon®YM3), gel filtration on, e.g., suitable Sephadex® gels or by HPLC on silica gel or reverse-phase material.

In the case of neutral complex compounds, it is often advantageous to pour the oligomeric complexes over an anion exchanger, for example IRA 67 (OH⁻ form), and optionally in addition over a cation exchanger, for example IRC 50 (H⁺ form), for separating ionic components.

The synthesis of the compounds of general formula I', i.e., the linkage of complexing agents to compounds of formula I", is carried out just like the coupling of metal complexes of general formula K' to the compounds of general formula I" analogously to the methods that are known in the literature, as they are described in, e.g., U.S. Pat. No. 5,135,737, H. Takalo et al., Bioconjugate Chem. 1994, 5, 278; EP 0430863; EP 0331616; WO 96/01655; EP 0271 180; U.S. Pat. No. 5,364,613; WO 95/17451 and WO 96/02669. It is carried out in solvents such as, e.g., water, methylene chloride, acetonitrile, chloroform, DMSO, pyridine, ethanol/water, ethanol/acetonitrile, dioxane, DMF, THF, lower alcohols, tetramethylurea, N-methylpyrrolidone, polyethylene glycols, 1,2-dimethoxyethane, dimethylacetamide, formamide, 1,2-dichloroethane or—if possible—their mixtures with water at temperatures of −10° C. to 100° C., preferably 0 to 50° C., especially preferably at room temperatures within 5 minutes to 72 hours, preferably 1 to 24 hours, especially preferably 1 to 14 hours, optionally with the addition of an organic or inorganic base, such as, e.g., aromatic or aliphatic amines, alkali- or alkaline-earth hydroxides, -carbonates or -bicarbonates, and quaternary ammonium hydroxides. By way of example, there can be mentioned triethylamine, diisopropyl-N-ethylamine (Hunig base), N-methylmorpholine, tributylamine, tetramethylethylenediamine, pyridine, lutedine, 2,4,6-trimethylpyridine, 4-dimethylaminopyridine, N-methylimidazole, tetramethylguanidine, DBU, lithium-, sodium-, potassium-, calcium-, magnesium-, barium hydroxide, -carbonate, -bicarbonate. The reaction can also be carried out in the buffer solutions that are known to one skilled in the art, preferably at pH 8 to 11, especially preferably at pH 8.5 to 9. The observance of pH value range is preferably done using a pH-stat.

If the coupling is done with a metal complex, dimethyl sulfoxide is preferably used as a solvent. In this case, it has proven advantageous to use salts such as, e.g., lithium chloride, sodium bromide, lithium bromide and lithium iodide as solubility-enhancing additives.

If the coupling is performed with a carboxyl group that is activated in situ, coupling reagents that are known to one skilled in the art, such as, e.g., DCCI, EEDQ, Staab reagent, BOP, PyBOP, TBTU, TDBTU, HBTU (see, e.g., Fournic-Zaluski et al., J. Med. Chem. 1996, 39, 2596; Houben-Weyl, Volume XV/2, Part II, 1974; Y. M. Angell et al., Tetrahedron Letters 1994, 35, 5981; L. A. Carpino et al., J. Chem. Soc. Commun. 1994, 201; H -O. Kim et al., Tetrahedron Letters 1995, 36, 6013; D. Papaioannou et al., Tetrahedron Letters, 1995, 36, 5187, G. Stemple et al., Bioorg. Med. Letters 1996, 6, 55, can be used.

The activated complexes or complexing agents V', VI', VII', VIII' and VIII'a that are used as starting substances

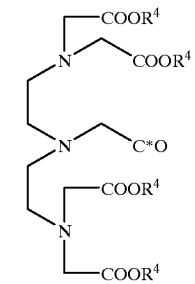

(VII')

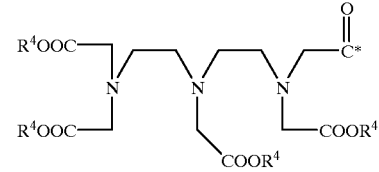

(VIII')

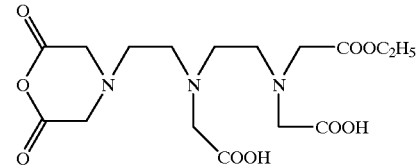

(VIII'a)

are known in the literature or can be obtained analogously to methods that are known in the literature:

VIII' and VIII'a, see, e.g., EP 263 059, VII', see, e.g., DE 19507822, DE 19580858, DE 19507819, V' and VI', see, e.g., U.S. Pat. No. 5,053,503, WO 96/02669, WO 96/01655, EP 0430863, EP 255471, U.S. Pat. No. 5,277,895, EP 0232751, U.S. Pat. No. 4,885,363.

The starting substances of general formula I" are obtained from compounds of general formula I A

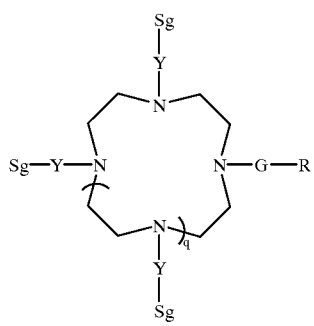

(IA)

which Sg stands for an amino protective group.

As amino protective groups, the benzyloxycarbonyl, tert-butoxycarbonyl, trifluoroacetyl, fluorenylmethoxycarbonyl, benzyl, formyl, 4-methoxybenzyl, 2,2,2-trichloroethoxycarbonyl, phthaloyl, 1,2-oxazolin, tosyl, dithiasuccinoyl, allyloxycarbonyl, sulfate, pent-4-enecarbonyl, 2-chloroacetoxymethyl (or -ethyl) benzoyl, tetrachlorophthaloyl, and alkyloxycarbonyl groups that are familiar to one skilled in the art can be mentioned [Th. W. Greene, P. G. M. Wuts, Protective Groups in Organic Syntheses, 2nd ed., John Wiley and Sons (1991), pp. 309–385; E. Meinjohanns et al., J. Chem. Soc. Pekin Trans 1, 1995, 405; U. Ellensik et al., Carbohydrate Research 280, 1996, 251; R. Madsen et al., J. Org. Chem. 60, 1995, 7920; R. R. Schmidt, Tetrahedron Letters 1995, 5343].

The cleavage of the protective groups is done according to the processes that are known to one skilled in the art (see, e.g., E. Wünsch, Methoden der Org. Chemie, Houben-Weyl, Volume XV/1, 4th Edition 1974, p. 315), for example by hydrolysis, hydrogenolysis, alkaline saponification of the esters with alkali in aqueous-alcoholic solution at temperature of 0° C. to 50° C., acid saponification with mineral acids or in the case of Boc groups with the aid of trifluoroacetic acid.

The production of the protected macrocycles of general formula I A can be carried out by acylation of compounds of general formula IB

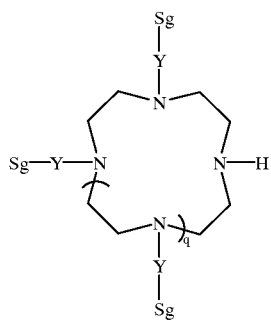

(IB)

with a substrate, introducing the desired substituents, of general formula IC

Nu-G-R    (IC)

in which Nu stands for a nucleofuge.

Advantageously used as nucleofuges are the radicals:

F, Cl, Br, I, —OTs, —OMs, OH,

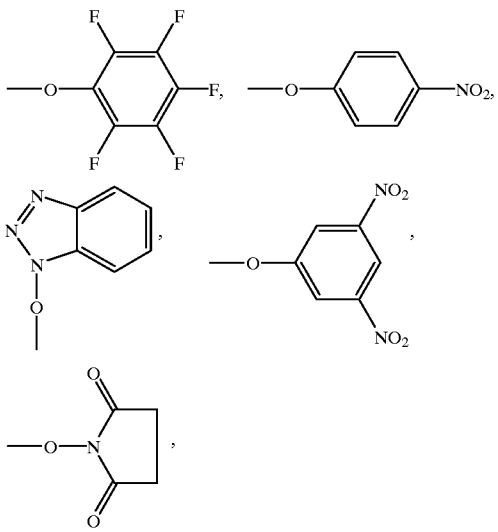

The reaction is performed in a mixture of water and organic solvents, such as isopropanol, ethanol, methanol, butanol, dioxane, tetrahydrofuran, dimethylformamide, dimethylacetamide, formamide or dichloromethane. Preferred are ternary mixtures that consist of water, isopropanol and dichloromethane.

The reaction is performed at a temperature range of between −10° C. and 100° C., preferably between 0° C. and 30° C.

As acid traps, inorganic and organic bases, such as triethylamine, pyridine, N-methylmorpholine, diisopropylethylamine, dimethylaminopyridine, alkali and alkaline-earth hydroxides, their carbonates or bicarbonates such as lithium hydroxide, sodium hydroxide, potassium hydroxide, sodium carbonate, sodium bicarbonate and potassium bicarbonate, are used.

If Nu stands for an OH group, the coupling reagents that are known to one skilled in the art, such as, e.g., DCCI, EEDQ, Staab reagent, BOP, PyBOP, TBTU, TDBTU, HBTU (see, e.g., Fournic-Zaluski et al., J. Med. Chem. 1996, 39, 2596; Houben-Weyl, Volume XV/2, Part II, 1974; Y. M. Angell et al., Tetrahedron Letters 1994, 35, 5981; L. A. Carpino et al., J. Chem. Soc. Commun. 1994, 201; H -O. Kim et al., Tetrahedron Letters 1995, 36, 6013; D. Papaioannou et al, Tetrahedron Letters, 1995, 36, 5187, G. Stemple et al., Bioorg. Med. Letters 1996, 6, 55, can be used.

The production of compounds IB that are required for the above-mentioned acylation reaction as educts is described in DE-OS 19549286.

The synthesis of the compounds of general formula IC is done according to the methods that are known to one skilled in the art and is adequately described in the examples.

Another possible synthesis of the macrocycles of general formula IA consists in the fact that compounds of general formula IE

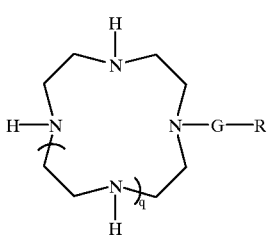

are reacted with compounds, known in the literature, of general formula ID

Nu-Y-Sg    (ID)

in a way that is known to one skilled in the art, as described in the reaction of IB with IC.

The above-mentioned compound of general formula IE is obtained by cleavage of amino protective groups from compounds of general formula IF,

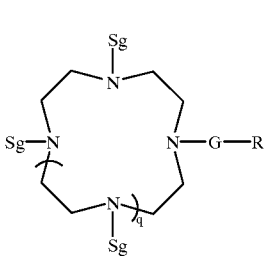

which are accessible from the compounds of general formula IG that are known in the literature.

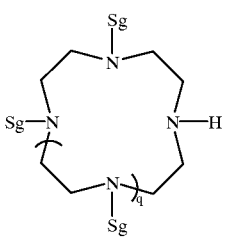

The latter can be obtained by acylation with substrates of general formula IC analogously to the above-described reaction of IB with IC.

The production of the pharmaceutical agents according to the invention is carried out in a way that is known in the art, by the complex compounds according to the invention—optionally with the addition of the additives that are commonly used in galenicals—being suspended or dissolved in aqueous medium, and then the suspension or solution optionally being sterilized. Suitable additives are, for example, physiologically harmless buffers (such as, for example, tromethamine), additives of complexing agents or weak complexes (such as, for example, diethylenetriamine-pentaacetic acid or the Ca-oligomer complexes that correspond to the metal complexes according to the invention) or—if necessary—electrolytes, such as, for example, sodium chloride or—if necessary—antioxidants, such as, for example, ascorbic acid.

If suspensions or solutions of the agents according to the invention in water or physiological salt solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween®, Myrj®] and/or flavoring substance(s) for taste correction [for example, ethereal oils].

In principle, it is also possible to produce the pharmaceutical agents according to the invention without isolating the complexes. Special care must always be taken to perform the chelation to ensure that the complexes according to the invention are virtually free of uncomplexed metal ions that have a toxic action.

This can be ensured with the aid of, for example, color indicators such as xylenol orange by control titration during the production process. The invention therefore also relates to the process for the production of complex compounds and their salts. As a final precaution, there remains purification of the isolated complex.

The pharmaceutical agents according to the invention preferably contain 0.1 μmol–1 mol/l of the complex and are generally dosed in amounts of 0.0001–5 mmol/kg. They are intended for enteral and parenteral administration. The complex compounds according to the invention are used 1. for NMR diagnosis and diagnostic radiology in the form of complexes of them with the ions of elements with atomic numbers 21–29, 42, 44 and 57–83;
2. for radiodiagnosis and radiotherapy in the form of complexes of them with the radioisotopes of elements with atomic numbers 27, 29, 31, 32, 37–39, 43, 49, 62, 64, 70, 75 and 77.

The agents according to the invention meet the varied requirements for suitability as contrast media for nuclear spin tomography. They are thus extremely well suited for improving the image, obtained with the aid of the nuclear spin tomograph, as regards its informational value after oral or parenteral administration by increasing the signal intensity. They also show the great effectiveness that is necessary to burden the body with the smallest possible amounts of foreign substances, and the good compatibility that is necessary to preserve the noninvasive nature of the studies.

The good water solubility and low osmolality of the agents according to the invention make it possible to produce highly concentrated solutions, i.e., to keep the volume load on the circulation within reasonable bounds and to offset the dilution by bodily fluids. In addition, the agents according to the invention have not only high stability in vitro, but also surprisingly high stability in vivo, so that release or exchange of the ions that are not covalently bonded—and that are inherently toxic—in the complexes occurs only extremely slowly within the time during which the contrast media are completely eliminated again.

In general, the agents according to the invention for use as NMR diagnostic agents are dosed in amounts of 0.0001–5 mmol/kg, preferably 0.005–0.5 mmol/kg. Details on use are discussed in, for example, H. -J. Weinmann et al., Am. J. of Roentgenology 142, 619 (1984).

Especially low dosages (below 1 mg/kg of body weight) of organ-specific NMR diagnostic agents can be used, for example, for detecting tumors and myocardial infarction.

The complex compounds according to the invention can also be used advantageously as susceptibility reagents and as shift reagents for in-vivo-NMR spectroscopy.

Owing to their advantageous radioactive properties and the good stability of the complex compounds contained therein, the agents according to the invention are also suitable as radiodiagnostic agents. Details on their use and dosage are described in, e.g., "Radiotracers for Medical Applications," CRC Press, Boca Raton, Fla.

Another imaging method with radioisotopes is positron-emission tomography, which uses positron-emitting isotopes, such as, e.g., $^{43}$Sc, $^{44}$Sc, $^{52}$Fe, $^{55}$Co and $^{68}$Ga (Heiss, W. D.; Phelps, M. E.; Positron Emission Tomography of Brain, Springer Verlag Berlin, Heidelberg, New York 1983).

The compounds according to the invention are also suitable, surprisingly enough, for differentiating malignant and benign tumors in areas without blood-brain barriers.

They are also distinguished in that they are completely eliminated from the body and are well tolerated.

Since the substances according to the invention accumulate in malignant tumors (no diffusion in healthy tissue, but high permeability of tumor vessels), they can also support the radiation therapy of malignant tumors. The latter are distinguished from the corresponding diagnosis only by the amount and type of the isotope used. In this case, the goal is the destruction of tumor cells by high-energy shortwave radiation with a smallest possible range of action. For this purpose, interactions of the metals that are contained in the complexes (such as, e.g., iron or gadolinium) with ionizing radiations (e.g., x rays) or with neutron rays are employed. The local radiation dose at the site where the metal complex is located (e.g., in tumors), is significantly enhanced by this effect. To produce the same radiation dose in malignant tissue, the radiation exposure for healthy tissue can be considerably reduced and thus burdensome side effects for the patients can be avoided when such metal complexes are used. The compounds according to the invention are therefore also suitable as radiosensitizing substances in treating malignant tumors by radiation (e.g., exploiting Mössbauer effects or in neutron capture therapy). Suitable β-emitting ions are, for example, $^{46}$Sc, $^{47}$Sc, $^{48}$Sc, $^{72}$Ga, $^{73}$Ga and $^{90}$Y. Suitably short half-lives that have α-emitting ions are, for example, $^{211}$Bi, $^{212}$Bi, $^{213}$Bi and $^{214}$Bi, whereby $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy that is proposed by R. L. Mills et al. (Nature Vol. 336, (1988), p. 787], the central ion must be derived from a Mössbaure isotope, such as, for example, $^{57}$Fe or $^{151}$Eu.

In in-vivo administration of the therapeutic agents according to the invention, the latter can be administered together with a suitable vehicle, such as, for example, serum or physiological common salt solution and together with another protein such as, for example, human serum albumin. In this case, the dosage depends on the type of cellular disruption, the metal ion used and the type of imaging method.

The therapeutic agents according to the invention are administered parenterally, preferably i.v.

Details on the use of radiotherapeutic agents are discussed in, e.g., R. W. Kozak et al., TIBTEC, October 1986, 262.

The agents according to the invention are extremely well suited as x-ray contrast media, whereby especially to be emphasized is that with them, no signs of the anaphylaxis-like reactions that are known from the iodine-containing contrast media can be detected in biochemical-pharmacological studies. They are especially valuable owing to their advantageous absorption properties in ranges of higher tube voltages for digital subtraction techniques.

In general, the agents according to the invention for use as x-ray contrast media are dosed analogously to, for example, meglumine-diatrizoate in amounts of 0.1–5 mmol/kg, preferably 0.25–1 mmol/kg.

Details on the use of x-ray contrast media are discussed in, for example, Barke, Röntgenkontrastmittel [X-Ray Contrast Media], G. Thieme, Leipzig (1970) and P. Thurn, E. B ücheler "Einführung in die Röntgendiagnostik," G. Thieme, Stuttgart, New York (1977).

In summary, it has been possible to synthesize new compounds that open up new possibilities in diagnostic and therapeutic medicine.

The examples below are used for a more detailed explanation of the object of the invention. In this case, the following abbreviations were used:

a) DTPA-monoanhydrise-ethyl ester:

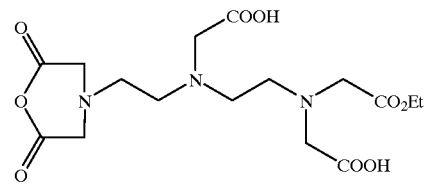

b) sym-DTPA-tetra-t.butylester:

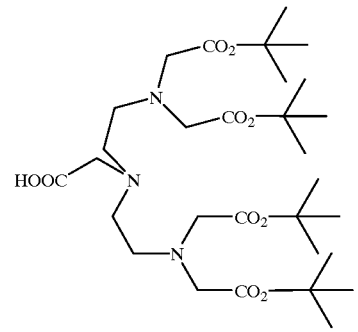

c) Gly-methyl-DOTA-tri-t.butylester (sodium bromide complex)

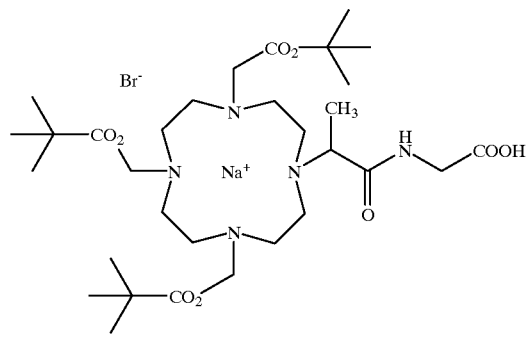

EXAMPLE 1 a) 3-(Bis(N-t.butyloxycarbonylmethyl)-6-[N-(3-aza-2-oxo-4-carboxy)-butyl]-3,6,9-triaza-undecane-1,11-dicarboxylic acid-di-t.butylester 50 g (81 mmol) of sym.-DTPA-tetra-t.butylester and 11.2 g (97 mmol) of N-hydroxysuccinimide are dissolved in 300 ml of dimethylformamide and cooled to 0° C. 20.6 g (100 mmol) of dicyclohexylcarbodiimide is added, and it is stirred for 30 minutes at 0° C., then for 2 hours at room temperature. It is cooled to 0° C., and 5.25 g (70 mmol) of glycine is added, then 20.2 g (200 mmol) of triethylamine, and it is allowed to come slowly to room temperature (about 4 hours). It is evaporated to the dry state in a vacuum, the residue is taken up in 400 ml of methylene chloride, and urea is filtered out. The filtrate is extracted 3 times with an aqueous hydrochloric acid (pH 3, 600 ml each), dried on magnesium sulfate and evaporated to the dry state. The residue is chromatographed in silica gel (mobile solvent: methylene chloride/MeOH=20:1+2% acetic acid). The product-containing fractions are evaporated to the dry state in a vacuum, and the residue is recrystallized from methyl-t.butyl ether.

Yield: 43 g (91% of theory) of a colorless crystalline solid
Analysis: Cld: C 56.96 H 8.66 N 8.30; Fnd: C 56.75 H 8.33 N 8.13;

b) 1,4,7-Tris{3,9-bis(N-t.butyloxycarbonylmethyl)-6-[N-(3-aza-2,5-dioxo-)-pentane-1,5-diyl]-3,6,9-triazaundecanedioic acid-di-t.butylester}-1,4,7,10-tetraazacyclododecane 40 g (59.27 mmol) of the title compound of Example 1a and 3.09 g (17.96 mmol) of cyclene (=1,4,7,10-tetraazacyclododecane) are dissolved in 300 ml of dimethylformamide, and 19.8 g (80 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel. (Mobile solvent: methylene chloride/2-propanol=20:1).

Yield: 11.93 g (31% of theory) of a colorless, viscous oil.
Analysis: Cld: C 58.30 H 8.84 N 10.46; Fnd: C 58.12 H 9.05 N 10.25;

C) 1,4,7-Tris{3,9-bis(N-t.butyloxycarbonylmethyl)-6-[N-(3-aza-2,5-dioxo-pentane-1,5-diyl]-3,6,9-triazaundecanedioic acid-di-t.butylester}-10-[N-(n hexadecanoyl]-1,4,7,10-tetraazacyclododecane 10 g (4.67 mmol) of the title compound of Example 1b and 2.93 g (9.33 mmol) of hexadecanoic acid are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel. (Mobile solvent: methylene chloride/2-propanol=25:1).

Yield: 10.12 g (91% of theory) of a colorless, viscous oil.
Analysis: Cld: C 60.53 H 9.23 N 9.41; Fnd: C 60.31 H 9.40 N 9.27;

d) 1,4,7-Tris{3,9-bis(N-carboxylatomethyl)-6-[N-(3-aza-2,5-dioxo-pentane-1,5-diyl)-3,6,9-triazaundecane-1-carboxylato-11-acid, Gd complex, monosodium salt}-10-[N-(n hexadecanoyl]-1,4,7,10-tetraazacyclododecane 10 g (4.2 mmol) of the title compound of Example 1c is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 $\mu$S. Then, the contents of the ultrafiltration cell are freeze-dried.

Yield: 9.02 g (96% of theory) of a colorless, amorphous powder Water content: 10.1%; Analysis (calculated based on anhydrous substance): Cld: C 38.67 H 4.96 N 10.02 Gd 21.09 Na 3.08; Fnd: C 38.41 H 5.18 N 9.85 Gd 20.84 Na 2.84; Relaxivity $R_1$ (l•mmol$^{-1}$s$^{-1}$) in plasma (20 MH$_z$, 40° C.,0.47 Tesla):21.2.

EXAMPLE 2 a) 1,4,7-Tris{3,9-bis(N-t.butyloxycarbonylmethyl)-6-[N-3-aza-2,5-dioxo-pentane-1,5-diyl]-3,6,9-triazaundecanedioic acid-di-t.butylester}-10-[N-(n pentadecanoyl)]-1,4,7,10-tetraazacyclododecane 10 g (4.67 mmol) of the title compound of Example 1b and 2.26 g (9.33 mmol) of pentadecanoic acid are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1).

Yield: 10.2 g (92 of theory) of a colorless, viscous oil
Analysis: Cld: C 60.38 H 9.20 N 9.47; Fnd: C 60.17 H 9.35 N 9.31;

b) 1,4,7-Tris{3,9-bis(N-carboxylatomethyl)-6-[N-(3-aza-2,5-dioxo-pentane-1,5-diyl)]-3,6,9-triazaundecane-1-carboxylato-11-acid, Gd complex, monosodium salt}-10-[N-(n pentadecanoyl)]-1,4,7,10-tetraazacyclododecane 9.94 g (4.2 mmol) of the title compound of Example 2a is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 $\mu$S. Then, the contents of the ultrafiltration cell are freeze-dried.

Yield: 9.05 g (97% of theory) of a colorless, amorphous powder Water content: 9.8%; Analysis (calculated based on anhydrous substance): Cld: C 38.37 H 4.90 N 10.08 Gd 21.23 Na 3.10; Fnd: C 38.15 H 5.11 N 9.87 Gd 21.03 Na 2.85;

EXAMPLE 3 a) 1,4,7-Tris{3,9-bis(N-t.butyloxycarbonylmethyl)-6-[N-(3-aza-2,5-dioxo-pentane-1,5-diyl)]-3,6,9-triazaundecanedioic acid-di-t.butylester}-10-[N-(n tetradecanoyl)]-1,4,7,10-tetraazacyclododecane 10 g (4.67 mmol) of the title compound of Example 1b and 2.13 g (9.33 mmol) of tetradecanoic acid are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1).

Yield: 10 g (91% of theory) of a colorless, viscous oil.
Analysis: Cld: C 60.23 H 9.17 N 9.52; Fnd: C 60.04 H 9.33 N 9.36;

b) 1,4,7-Tris{3,9-bis(N-carboxylatomethyl)-6-[N-(3-aza-2,5-dioxo-pentane-1,5-diyl)]-3,6,9-triazaundecane-1-carboxylato-11-acid, Gd complex, monosodium salt}-10-[N-(n tetradecanoyl)]-1,4,7,10-tetraazacyclododecane 9.88 g (4.2 mmol) of the title compound of Example 3a is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 $\mu$S. Then, the contents of the ultrafiltration cell are freeze-dried.

Yield: 8.90 g (96% of theory) of a colorless, amorphous powder Water content: 11.0%; Analysis (calculated based on anhydrous substance): Cld: C 38.07 H 4.84 N 10.15 Gd 21.36 Na 3.12; Fnd: C 37.84 H 4.97 N 9.93 Gd 21.14 Na 2.80; Relaxivity $R_1$ (l•mmol$^{-1}$s$^{-1}$) in plasma (20 MHz,40° C.,0.47 Tesla):19.2

EXAMPLE 4

1,4,7-Tris{3,9-bis(N-carboxylatomethyl)-6-[N-3-aza-2,5-dioxo-pentane-1,5-diyl]-3,6,9-triazaundecane-1-carboxylato-11-acid, Dy complex, monosodium salt}-10-[N-(n-hexadecanoyl]-1,4,7,10-tetraazacyclododecane 10 g (4.2 mmol) of the title compound of Example 1c is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.35 g (6.3 mmol) of dysprosium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 µS. Then, the contents of the ultrafiltration cell are freeze-dried.

Yield: 8.18 g (93% of theory) of a colorless, amorphous powder Water content: 7.8%; Analysis (calculated based on anhydrous substance):

Cld: C 38.40 H 4.92 N 9.95 Dy 21.65 Na 3.06. Fnd: C 38.20 H 5.13 N 9.84 Dy 21.43 Na 2.85;

EXAMPLE 5

1,4,7-Tris{3,9-bis(N-carboxylatomethyl)-6-[N-3-aza-2,5-dioxo-pentane-1,5-diyl]-3,6,9-triazaundecane-1-carboxylato-11-acid, Yb complex, monosodium salt}-10-[N-(n-pentadecanoyl]-1,4,7,10-tetraazacyclododecane 10 g (4.2 mmol) of the title compound of Example 1c is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 3.31 g (6.3 mmol) of ytterbium carbonate is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 µS. Then, the contents of the ultrafiltration cell are freeze-dried.

Yield: 9.02 g (94% of theory) of a colorless, amorphous powder Water content: 9.1%; Analysis (calculated based on anhydrous substance): Cld: C 37.87 H 4.85 N 9.81 Yb 22.73 Na 3.02; Fnd: C 37.61 H 5.09 N 9.62 Yb 22.50 Na 2.76;

EXAMPLE 6

1,4,7-Tris{3,9-bis(N-carboxylatomethyl)-6-[N-3-aza-2,5-dioxo-pentane-1,5-diyl]-3,6,9-triazaundecane-1-carboxylato-11-acid, Eu complex, monosodium salt}-10-[N-(n-tetradecanoyl)]-1,4,7,10-tetraazacyclododecane 10 g (4.2 mmol) of the title compound of Example 1c is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 3.05 g (6.3 mmol) of europium carbonate is added, and it is stirred for 2 hours at 70° C. It is cooled to room temperature and set at pH 7.2 with 10% aqueous sodium hydroxide solution.

The solution is mixed with 2 g of activated carbon, cooled for 1 hour at room temperature and filtered. The filtrate is loaded into an ultrafiltration cell and dialyzed (Amicon® YM1). Dialysis is performed until the eluate has reached a conductivity of 10 µS. Then, the contents of the ultrafiltration cell are freeze-dried.

Yield: 8.67 g (93% of theory) of a colorless, amorphous powder Water content: 9.3%; Analysis (calculated based on anhydrous substance): Cld: C 38.94 H 4.99 N 10.09 Eu 20.53 Na 3.11; Fnd: C 38.75 H 5.18 N 9.87 Eu 20.31 Na 2.84;

EXAMPLE 7 a) Heptanoic acid-N-(10-carboxy)-decylamide 10 g (49.7 mmol) of 11-aminoundecanoic acid is suspended in a mixture of 100 ml of tetrahydrofuran/100 ml of water, and the pH is brought to 10 by adding 10% aqueous sodium hydroxide solution. It is cooled to 0° C., and 8.86 g (59.6 mmol) of n-heptanoic acid chloride, dissolved in 50 ml of tetrahydrofuran, is added in drops within 30 minutes. In this case, the pH is kept between 9–10 by simultaneous addition of sodium hydroxide solution. Then, it is stirred for 1 hour at room temperature. It is acidified with 10% aqueous hydrochloric acid (pH 1), 200 ml of ethyl acetate is added, and the organic phase is separated. The organic phase is washed with 100 ml of saturated common salt solution, dried on magnesium sulfate and evaporated to the dry state in a vacuum. The residue is recrystallized from diethyl ester.

Yield: 13.87 g (89% of theory) of a colorless, waxy solid. Analysis: Cld: C 68.97 H 11.25 N 4.47; Fnd: C 68.75 H 11.38 N 4.29;

b) 1,4,7-Tris{3,9-bis(N-t.butyloxycarbonylmethyl)-6-[N-(3-aza-2,5-dioxo-pentane-1,5-diyl)]-3,6,9-triazaundecanedioic acid-di-t.butylester}-10-[N-(12-aza-13-oxo)-nonadecanoyl]-1,4,7,10-tetraazacyclododecane 10 g (4.67 mmol) of the title compound of Example 1b and 2.92 g (9.33 mmol) of the title compound of Example 7a are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1).

Yield: 10.47 g (92% of theory) of a colorless, viscous oil Analysis: Cld: C 60.10 H 9.14 N 9.77; Fnd: C 59.91 H 9.36 N 9.63;

c) 1,4,7-Tris{3,9-bis(N-carboxylatomethyl)-6-(N-(3-aza-2,5-dioxo-pentane-1,5-diyl)]-3,6,9-triazaundecane-1-carboxylato-11-acid, Gd complex, monosodium salt}-10-[N-(12-aza-13-oxo)-monodecanoyl]-1,4,7,10-tetraazacyclododecane 10.24 g (4.2 mmol) of the title compound of Example 7b is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 µS. Then, the contents of the ultrafiltration cell are freeze-dried.

Yield: 8.96 g (93% of theory) of a colorless, amorphous powder Water content: 9.4%; Analysis (calculated based on anhydrous substance): Cld: C 38.75 H 4.97 N 10.38 Gd 20.57 Na 3.01; Fnd: C 38.58 H 5.18 N 10.15 Gd 20.39 Na 2.78;

EXAMPLE 8 a) 4-(11-Oxaundecyl)-benzoic acid 38.83 g (144.8 mmol) of decyl iodide is added to a mixture of 20 g (144.8 mmol) of 4-hydroxybenzoic acid and 46 g (434.4 mmol) of sodium carbonate in 400 ml of dimethylformamide, and it is heated for 4 hours to 70° C. Solid is filtered out, the filtrate is evaporated to the dry state in a vacuum, and the residue is taken up in 300 ml of methylene chloride, and 300 ml of 5% aqueous hydrochloric acid is added. It is thoroughly stirred, the organic phase is separated, and it is dried on magnesium sulfate. Then, the organic phase is evaporated to the dry state. The residue is chromatographed on silica gel (mobile solvent: n-hexane-acetone=20:1).

Yield: 15.31 g (38% of theory) of a colorless, vitreous solid Analysis: Cld: C 73.35 H 9.41; Fnd: C 73.17 H 9.65;

b) 1,4,7-Tris{3,9-bis(N-t.butyloxycarbonylmethyl)-6-[N-(3-aza-2,5-dioxo-pentane-1,5-diyl)]-3,6,9-triazaundecanedioic acid-di-t.butylester}-10-<N-[4-(11-oxaundecyl)]-benzoyl>1,4,7,10-tetraazacyclododecane 10 g (4.67 mmol) of the title compound of Example 1b and 2.60 g (9.33 mmol) of the title compound of Example 8a are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 10.32 g (92% of theory) of a colorless, viscous solid Water content: 9.4%; Analysis: Cld: C 60.48 H 8.89 N 9.33; Fnd: C 60.29 H 8.71 N 9.15;

c) 1,4,7-Tris[3,9-bis(N-carboxylatomethyl)-6-[N-(3-aza-2,5-dioxo-pentane-1,5-diyl)]-3,6,9-triazaundecane-1-carboxylato-11-acid, Gd complex, monosodium salt}-10-[N-4-(11-oxaundecyl)-benzoyl]-1,4,7,11-tetraazacyclododecane 10.1 g (4.2 mmol) of the title compound of Example 8b is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 $\mu$S. Then, the contents of the ultrafiltration cell are freeze-dried.

Yield: 9.2 g (94% of theory) of a colorless, amorphous powder Water content: 7.9%; Analysis (calculated based on anhydrous substance): Cld: C 38.82 H 4.64 N 9.92 Gd 20.89 Na 3.05; Fnd: C 38.63 H 4.78 N 9.70 Gd 20.64 Na 2.81;

EXAMPLE 9 a) 11-Bromoundecanoic acid-benzyl ester 30 g (113.1 mmol) of 11-bromoundecanoic acid, 18.35 g (169.7 mmol) of benzyl alcohol and 0.5 g of p-toluenesulfonic acid are heated in 200 ml of toluene for 12 hours in a water separator. It is allowed to reach room temperature, and the organic phase is washed twice with 100 ml of 5% aqueous potassium carbonate solution each. The organic phase is dried on magnesium sulfate and concentrated by evaporation in a vacuum. The residue is chromatographed on silica gel (mobile solvent: n-hexane/acetone=30:1).

Yield: 32.55 g (81% of theory) of a colorless oil Analysis: Cld: C 60.85 H 7.66 Br 22.49; Fnd: C 60.64 H 7.83 Br 22.31;

b) 11-(4-Methylphenyl)-11-oxaundecanoic acid benzyl ester 32 g (90 mmol) of the title compound of Example 9a is added to a mixture of 9.73 g (90 mmol) of 4-hydroxy-toluene and 37.32 g (270 mmol) of potassium carbonate in 200 ml of dimethylformamide, and it is heated for 4 hours to 70° C. Solid is filtered out, the filtrate is evaporated to the dry state in a vacuum, and the residue is taken up in 300 ml of methylene chloride, and 200 ml of 5% aqueous hydrochloric acid is added. It is thoroughly stirred, the organic phase is separated, and it is dried on magnesium sulfate. Then, the organic phase is evaporated to the dry state. The residue is chromatographed on silica gel (mobile solvent=n-hexane-acetone=30:1).

Yield: 26.5 g (77% of theory) of a colorless, viscous oil. Analysis: Cld: C 78.49 H 8.96; Fnd: C 78.49 H 8.96;

c) 11-(4-Methylphenyl)-11-oxaundecanoic acid 26 g (68 mmol) of the title compound of Example 9b is dissolved in 300 ml of 2-propanol, and 4 g of palladium catalyst (10% Pd/C) is added. It is hydrogenated overnight at room temperature. Catalyst is filtered out, and the filtrate is evaporated to the dry state in a vacuum.

Yield: 19.87 g (quantitative) of a vitreous, colorless solid. Analysis: Cld: C 73.93 H 9.65; Fnd: C 73.70 H 9.74;

d) 1,4,7-Tris{3,9-bis(N-t.butyloxycarbonylmethyl)-6-[N-(3-aza-2,5-dioxo-pentane-1,5-diyl)]-3,6,9-triazaundecanedioic acid-di-t.butylester}-10-[N-(11-(4-methylphenyl)-11-oxaundecanoyl]-1,4,7,10-tetraazacyclododecane 10 g (4.67 mmol) of the title compound of Example 1b and 2.73 g (9.33 mmol) of the title compound of Example 9c is dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 10.61 g (94% of theory) of a colorless, viscous oil Analysis: Cld: C 60.62 H 8.92 N 9.27; Fnd: C 60.48 H 9.10 N 9.08;

e) 1,4,7-Tris{3,9-bis(N-carboxylatomethyl)-6-[N-(3-aza-2,5-dioxo-pentane-1,5-diyl)]-3,6,9-triazaundecane-1-carboxylato-11-acid, Gd complex, monosodium salt}-10-<N-[11-(4-methylphenyl)-11-oxaundecanoyl]>-1,4,7,10-tetraazacyclododecane 10.15 g (4.2 mmol) of the title compound of Example 9e is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 $\mu$S. Then, the contents of the ultrafiltration cell are freeze-dried.

Yield: 8.97 g (94% of theory) of a colorless, amorphous powder Water content: 9.2%; Analysis (calculated based on anhydrous substance): Cld: C 39.11 H 4.70 N 9.86 Gd 20.76 Na 3.04; Fnd: C 39.01 H 4.89 N 9.70 Gd 20.50 Na 2.73;

EXAMPLE 10 a) 4-(12-Oxadodecanoic acid benzyl ester)-benzoic acid 77.2 g (217.2 mmol) of the title compound of Example 9a is added to a mixture of 30 g (217.2 mmol) of 4-hydroxybenzoic acid and 90.05 g (651.6 mmol) of potassium carbonate in 400 ml of dimethylformamide, and it is heated for 4 hours to 70° C. Solid is filtered out, the filtrate is evaporated to the dry state in a vacuum, and the residue is taken up in 1000 ml of methylene chloride, and 500 ml of 5% aqueous hydrochloric acid is added. It is thoroughly stirred, the organic phase is separated, and it is dried on magnesium sulfate. Then, the organic phase is evaporated to the dry state. The residue is chromatographed on silica gel (mobile solvent: n-hexane/acetone=20:1).

Yield: 48.38 g (54% of theory) of a colorless, vitreous solid. Analysis: Cld: C 72.79 H 7.82; Fnd: C 72.58 H 7.97;

b) 1,4,7-Tris{3,9-bis(N-t.butyloxycarbonylmethyl)-6-[N-(3-aza-2,5-dioxo-pentane-1,5-diyl)]-3,6,9-triazaundecanedioic acid-di-t.butylester}-10-<N-[4-(12-oxadodecanoic acid-benzylester)]-benzoyl>-1,4,7,10-tetraazacyclododecane 20 g (9.34 mmol) of the title compound of Example 1b and 7.71 g (18.68 mmol) of the title compound of Example 10a are dissolved in 200 ml of dimethylformamide, and 7.42 g (30 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 22.04 g (93% of theory) of a colorless, viscous oil Analysis: Cld: C 61.07 H 8.66 N 8.83; Fnd: C 60.94 H 8.83 N 8.70;

c) 1,4,7-Tris{3,9-bis(N-t.butyloxycarbonylmethyl)-6-[N-(3-aza-2,5-dioxo-pentane-1,5-diyl)]-3,6,9-triazaundecanedioic acid-di-t.butylester}-10-<N-[4-(12-oxadodecanoic acid)]-benzoyl>-1,4,7,10-tetraazacyclododecane 20 g (7.88 mmol) of the title compound of Example 10b is dissolved in 300 ml of 2-propanol, and 4 g of palladium catalyst (10% Pd/C) is added. It is hydrogenated overnight at room temperature. Catalyst is filtered out, and the filtrate is evaporated to the dry state in a vacuum.

Yield: 19.2 g (quantitative) of a colorless, viscous oil. Analysis: Cld: C 59.88 H 8.73 N 9.16; Fnd: C 59.66 H 8.95 N 9.04;

d) 1,4,7-Tris{3,9-bis(N-carboxylatomethyl)-6-[N-(3-aza-2,5-dioxo-pentane-1,5-diyl)]-3,6,9-triazaundecane-1-carboxylato-11-acid, Gd complex, monosodium salt}-10-<N-[4—(12-oxadodecanoic acid, sodium salt)]-benzoyl>-1,4,7,10-tetraazacyclododecane 10.28 g (4.2 mmol) of the title compound of Example 10c is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 $\mu$S. Then, the contents of the ultrafiltration cell are freeze-dried.

Yield: 9.18 g (94% of theory) of a colorless, amorphous powder Water content: 7.8%; Analysis (calculated based on anhydrous substance): Cld: C 38.24 H 4.47 N 9.64 Gd 20.30 Na 3.96; Fnd: C 38.13 H 4.62 N 9.49 Gd 20.13 Na 3.59;

EXAMPLE 11 a) 1,4,7-Tris{N-[2,6-bis(benzyloxycarbonylamino)]-hexanoyl}-1,4,7,10-tetraazacyclododecane 92.13 g (180 mmol) of di-(benzyloxycarbonyl)-lysine-N-hydroxysuccinimide ester (=$Z_2$-LysNHSI) and 20.24 g (200 mmol) of triethylamine are added to 10 g (58 mmol) of 1,4,7,10-tetraazacyclododecane (=cyclene) in 700 ml of toluene, and it is refluxed for 12 hours. It is evaporated to the dry state in a vacuum, the residue is taken up in 1000 ml of dichloromethane, and the organic phase is washed twice with 5% aqueous sodium carbonate solution. The organic phase is dried on magnesium sulfate and evaporated to the dry state in a vacuum. The residue is chromatographed on silica gel (mobile solvent: ethyl acetate/ethanol=20:1).

Yield: 48.26 g (61% of theory) of a colorless foam. Elementary analysis: Cld: C 65.28 H 6.81 N 10.29; Fnd: C 65.15 H 6.97 N 10.10;

b) 1,4,7-Tris{N-[2,6-bis(benzyloxycarbonylamino)]-hexanoyl}-10-(N-hexadecanoyl)-1,4,7,10-tetraazacyclododecane 12.72 g (9.34 mmol) of the title compound of Example 11a and 4.79 g (18.68 mmol) of palmitic acid are dissolved in 100 ml of dimethylformamide, and 7.42 g (30 mmol) of 2-ethoxy-1-ethoxycarbonyl-1,2-dihydroquinoline is added at 0° C. It is stirred for 24 hours at room temperature.

It is evaporated to the dry state in a vacuum, and the residue is chromatographed on silica gel (mobile solvent: ethyl acetate/ethanol=25:1)

Yield: 14.2 g (95% of theory) of a colorless, viscous oil Analysis: Cld: C 67.56 H 7.69 N 8.75; Fnd: C 67.38 H 7.83 N 8.60;

c) 1,4,7-Tris-[N-(2,6-diamino)-hexanoyl]-10-(N-hexadecanoyl)-1,4,7,10-tetraazacyclododecane, hexahydrobromide 14 g (8.75 mmol) of the title compound of Example 11b is dissolved in 60 ml of acetic acid and added in drops to a 60° C. solution that consists of 150 ml of hydrogen bromide in glacial acetic acid (33%). It is stirred for 1 hour at 60° C. It is cooled to 0° C., and 1000 ml of diethyl ether is slowly added in drops while being stirred. The deposited precipitate is filtered, rewashed twice with 100 ml of ether and dried in a vacuum furnace (60° C.).

Yield: 10.87 g (97% of theory) of a cream-colored, crystalline solid Elementary analysis: Cld: C 39.39 H 7.24 N 10.94 Br 37.44; Fnd: C 39.28 H 7.35 N 10.81 Br 37.25;

d) 1,4,7-Tris{N-hexanoyl-2,6-bis<amino-N-acetyl-2-[3,9-bis(N-t.butyloxycarboxylmethyl)-6-yl-3,6,9-triazaundecane-1,11-dicarboxylic acid-di-t.butylester]>}-10-(N-hexadecanoyl)-1,4,7,10-tetraazacyclododecane 23.02 g (200 mmol) of N-hydroxysuccinimide and 30.9 g (150 mmol) of dicyclohexylcarbodiimide are added to 67.42 g (109.3 mmol) of sym.-DTPA-tetra-t.butylester, dissolved in 450 ml of dimethylformamide, at 0° C., and it is stirred for one hour at this temperature. Then, it is stirred for 3 hours at room temperature. 14 g (10.93 mmol) of the title compound of Example 11c and 30.4 g (300 mmol) of triethylamine are added to this solution. It is stirred for 24 hours at room temperature. The solution is evaporated to the dry state, and the residue is taken up in 600 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum.

The residue is chromatographed on silica gel (mobile solvent: dichloromethane/2-propanol=25:1).

Yield: 32.2 g (67% of theory) of a colorless, viscous oil Elementary analysis: Cld: C 60.69 H 9.27 N 8.93; Fnd: C 60.48 H 9.38 N 8.75;

e) 1,4,7-Tris{N-hexanoyl-2,6-bis<amino-N-acetyl-2-[3,9-bis(N-carboxylatomethyl)-6-yl-3,6,9-triazaundecane-1-carboxylato-11 acid, Gd complex, monosodium salt]>}-10-(N-hexadecanoyl)-1,4,7,10-tetraazacyclododecane 18.45 g (4.2 mmol) of the title compound of Example 11d is dissolved in 300 ml of trifluoroacetic acid, and it is stirred for 12 hours at room temperature. It is evaporated to the dry state in a vacuum. The residue is dissolved in 150 ml of water and set at pH 4 with 10% aqueous sodium hydroxide solution. Then, 4.56 g (12.6 mmol) of gadolinium oxide is added, and it is stirred for 2 hours at 70° C. It is cooled to room temperature and set at pH 7.2 with 10% aqueous sodium hydroxide solution. The solution is mixed with 4 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 $\mu$S. Then, the contents of the ultrafiltration cell are freeze-dried.

Yield: 16.2 g (94% of theory) of a colorless, amorphous powder Water content: 10.1%; Analysis (relative to anhydrous substance): Cld: C 36.87 H 4.62 N 9.56 Gd 22.99 Na 3.36; Fnd: C 36.65 H 4.78 N 9.38 Gd 22.75 Na 3.10; Relaxivity $R_1$ ($l \cdot mmol^{-1}s^{-1}$) in plasma (20 $MH_z$,40° C.,0.47 Tesla):15.9

EXAMPLE 12
1,4,7-Tris{N-hexanoyl-2,6-bis[amino-3,6,9-tris(carboxylatomethyl)-3,6,9-triazaundecan-1-oyl-11-acid, Gd complex, monosodium salt]}-10-(N-hexadecanoyl)-1,4,7,10-tetraazacyclododecane 41.5 g (109.3 mmol) of DTPA-monoanhydride-ethyl ester and 3 g (24.6 mmol) of 4-(dimethylamino)-pyridine are added to 14 g (10.93 mmol) of the title compound of Example 11c and 79.1 g (1000 mmol) of pyridine in 400 ml of dimethylformamide. It is stirred for 24 hours at 50° C. It is evaporated to the dry state in a vacuum, the residue is taken up in 400 ml of water and set at pH 13 with 3N aqueous sodium hydroxide. It is stirred for 6 hours at room temperature. It is set at pH 4 with 10% aqueous hydrochloric acid, and 21.94 g (65.6 mmol) of gadolinium acetate is added. Then, it is stirred for 1 hour at 60° C. It is allowed to cool to room temperature, set at pH 7.2 with 2N aqueous sodium hydroxide solution, and the solution is dialyzed in an ultrafiltration cell (Amicon® YM-1) (6 passes). The contents of the ultrafiltration cell are freeze-dried.

Yield: 40.8 g (91% of theory) Water content: 11.3%; Elementary analysis (relative to anhydrous substance): Cld: C 36.87 H 4.62 N 9.56 Gd 22.99 Na 3.36; Fnd: C 36.67 H 4.74 N 9.48 Gd 22.75 Na 3.12;

EXAMPLE 13
a) 1,4,7-Tris{N-hexanoyl-2,6-bis<amino-[1,4,7-tris(N-t.butyloxycarbonylmethyl)-10-(N-(1-methyl-3-aza-2,5-dioxo-pentane-1,5-diyl)]-1,4,7,10-tetraazacyclododecane>]}-10-N-hexadecanoyl)-1,4,7,10-tetraazacyclododecane 23.02 g (200 mmol) of N-hydroxysuccinimide and 30.9 g (150 mmol) of dicyclohexylcarbodiimide are added to 81.62 g (109.3 mmol) of Gly-methyl-DOTA-tri-t.butylester (sodium bromide complex), dissolved in 500 ml of dimethylformamide, at 0° C., and it is stirred for one hour at this temperature. Then, it is stirred for 3 hours at room temperature. 14 g (10.93 mmol) of the title compound of Example 11c and 30.4 g (300 mmol) of triethylamine are added to this solution. It is stirred for 24 hours at room temperature. The solution is evaporated to the dry state, and the residue is taken up in 600 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum. The residue is chromatographed on silica gel (mobile solvent: dichloromethane/methanol=25:1).

Yield: 37.3 g (75% of theory) of a colorless, viscous oil Elementary analysis: Cld: C 60.19 H 9.22 N 12.31; Fnd: C 60.05 H 9.41 N 12.18;

b) 1,4,7-Tris{N-hexanoyl-2,6-bis<amino-[1,4,7-tris(N-carboxylatomethyl)-10-[N-(1-methyl-3-aza-2,5-dioxo-pentane-1,5-diyl)]-1,4,7,10-tetraazacyclododecane, Gd complex]>}-10-(N-hexadecanoyl)-1,4,7,10-tetraazacyclododecane 19.11 g (4.2 mmol) of the title compound of Example 13a is dissolved in 300 ml of trifluoroacetic acid, and it is stirred for 12 hours at room temperature. It is evaporated to the dry state. The residue is dissolved in 150 ml of water and set at pH 3.3 with 5% aqueous sodium hydroxide solution. Then, 4.56 g (12.6 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 17.82 g (95% of theory) of a colorless, amorphous solid Water content: 9.6%; Elementary analysis (relative to anhydrous substance): Cld: C 41.96 H 5.73 N 12.55 Gd 21.13; Fnd: C 41.85 H 5.86 N 12.45 Gd 21.02;

EXAMPLE 14
a) 3,5-Bis[2-(benzyloxycarbonylamino)-acetylamino] benzoic acid 122.5 g (400 mmol) of N-(benzyloxycarbonyl)-glycine-N-hydroxysuccinimide ester is added to 30 g (197.2 mmol) of 3,5-diaminobenzoic acid and 59.85 g (591.5 mmol) of triethylamine in 400 ml of dimethylformamide, and it is stirred for 24 hours at room temperature. It is evaporated to the dry state in a vacuum, the residue is dissolved in 1000 ml of dichloromethane and extracted twice with 5% aqueous hydrochloric acid each. The organic phase is dried on magnesium sulfate and evaporated to the dry state. The residue is recrystallized from diisopropyl ether.

Yield: 95.92 g (91% of theory) of a crystalline solid Elementary analysis: Cld: C 60.67 H 4.90 N 10.48; Fnd: C 60.48 H 5.10 N 10.33;

b) 1,4,7-Tris{N-3,5-bis[(2-benzyloxycarbonylamino)-acetylamino]-benzoyl}-1,4,7,10-tetraazacyclododecane 90 g (168.4 mmol) of the title compound of Example 14a and 8.79 g (51 mmol) of 1,4,7,10-tetraazacyclododecane (=cyclene) are dissolved in 400 ml of dimethylformamide, and 74.2 g (300 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: ethyl acetate/ethanol=20:1)

Yield: 50.93 g (58% of theory) of a colorless solid Elementary analysis: Cld: C 62.08 H 5.39 N 13.02; Fnd: C 61.91 H 5.51 N 12.85;

c) 1,4,7-Tris{N-3,5-bis[(2-benzyloxycarbonylamino)-acetylamino]-benzoyl}-10-(N-tetradecanoyl)-1,4,7,10-tetraazacyclododecane 16.08 g (9.34 mmol) of the title compound of Example 14b and 3.81 g (16.68 mmol) of tetradecanoic acid are dissolved in 150 ml of dimethylformamide, and 7.42 g (30 mmol) of 2-ethoxy-1-ethoxycarbonyl-1,2-dihydroquinoline is added at 0° C. It is stirred for 24 hours at room temperature.

It is evaporated to the dry state in a vacuum, and the residue is chromatographed on silica gel (mobile solvent: ethyl acetate/ethanol=20:1)

Yield: 16.6 g (92% of theory) of a colorless, viscous oil
Analysis: Cld: C 64.03 H 6.16 N 11.60; Fnd: C 63.87 H 6.28 N 11.43;

d) 1,4,7-Tris{N-3,5-bis[(2-amino)-acetylamino]-benzoyl}-10-(N-tetradecanoyl)-1,4,7,10-tetraazacyclododecane, hexahydrobromide 15 g (7.76 mmol) of the title compound of Example 14c is dissolved in 70 ml of acetic acid and added in drops to a 60° C. solution that consists of 200 ml of hydrogen bromide in glacial acetic acid (33%). It is stirred for 1 hour at 60° C. It is cooled to 0° C., and 1000 ml of diethyl ether is slowly added in drops while being stirred. The deposited precipitate is filtered, rewashed twice with 100 ml of ether and dried in a vacuum furnace (60° C.).

Yield: 12.26 g (98 of theory) of a cream-colored, crystalline solid Elementary analysis: Cld: C 40.96 H 5.50 N 13.90 Br 29.73; Fnd: C 40.85 H 5.71 N 13.72 Br 29.41;

e) 1,4,7-Tris{N-3,5-bis<[1,4,7-tris(N-t.butyloxycarbonylaminomethyl)-1,4,7,10-tetraazacyclododecane-10-(N-4,7-diaza-3,6,9-trioxa-nonane-2,9-diyl)]amino>-benzoyl}-10-(N-tetradecanoyl)-1,4,7,10-tetraazacyclododecane 23.02 g (200 mmol) of N-hydroxysuccinimide and 30.9 g (150 mmol) of dicyclohexylcarbodiimide are added to 81.62 g (109.3 mmol) of Gly-methyl-DOTA-tri-t.butylester (sodium bromide complex), dissolved in 500 ml of dimethylformamide, at 0° C., and it is stirred for 1 hour at this temperature. Then, it is stirred for 3 hours at room temperature. 17.63 g (10.93 mmol) of the title compound of Example 14d and 30.4 g (300 mmol) of triethylamine are added to this solution. It is stirred for 24 hours at room temperature. The solution is evaporated to the dry state, and the residue is taken up in 600 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum. The residue is chromatographed on silica gel (mobile solvent= dichloromethane/methanol=25:1).

Yield: 40.02 g (75% of theory) of a colorless solid Elementary analysis: Cld: C 59.29 H 8.51 N 13.20; Fnd: C 59.05 H 8.75 N 13.01;

f) 1,4,7-Tris(N-3,5-bis<[1,4,7-tris-(N-carboxylatomethyl)-1,4,7,10-tetraazacyclododecane-10-(N-4,7-diaza-3,6,9-trioxa-nonane-2,9-diyl)]-amino>-benzoyl, Gd complex}-10-(N-tetradecanoyl)-1,4,7,10-tetraazacyclododecane 20.51 g (4.2 mmol) of the title compound of Example 14e is dissolved in 300 ml of trifluoroacetic acid, and it is stirred for 12 hours at room temperature. It is evaporated to the dry state. The residue is dissolved in 150 ml of water and set at pH 3.3 with 5% aqueous sodium hydroxide solution. Then, 4.56 g (12.6 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 18.94 g (94% of theory) of a colorless, amorphous solid Water content: 10.1%; Elementary analysis (relative to anhydrous substance): Cld: C 42.31 H 5.25 N 13.43 Gd 19.67; Fnd: C 42.17 H 5.41 N 13.28 Gd 19.45;

EXAMPLE 15 a) 1,4,7-Tris[N-(2-benzoyloxycarbonylamino)-acetyl]-1,4,7,10-tetraazacyclododecane 47.5 g (155 mmol) of N-(benzyloxycarbonyl)-glycine-N-hydroxysuccinimide ester and 25.3 g (250 mmol) of triethylamine are added to 8.79 g (51 mmol) of 1,4,7,10-tetraazacyclododecane (=cyclene) in 400 ml of toluene, and it is refluxed for 12 hours. It is evaporated to the dry state in a vacuum, the residue is taken up in 500 ml of dichloromethane, and the organic phase is washed twice with 5% aqueous sodium carbonate solution. The organic phase is dried on magnesium sulfate and evaporated to the dry state in a vacuum. The residue is chromatographed on silica gel (mobile solvent: ethyl acetate/ethanol=20:1).

Yield: 20.92 g (55% of theory) of a colorless foam. Elementary analysis: Cld: C 61.20 H 6.35 N 13.15; Fnd: C 61.03 H 6.48 N 13.02;

b) 1,4,7-Tris[N-(2-amino)-acetyl]-1,4,7,10-tetraazacyclododecane, tetrahydrobromide 20 g (26.82 mmol) of the title compound of Example 15a is dissolved in 100 ml of acetic acid and added in drops to a 60° C. solution that consists of 350 ml of hydrogen bromide in glacial acetic acid (33%). It is stirred for 1 hour at 60° C. It is cooled to 0° C., and 1500 ml of diethyl ether is slowly added in drops while being stirred. The deposited precipitate is filtered, rewashed twice with 200 ml of ether and dried in a vacuum furnace (60° C.).

Yield: 17.35 g (97 of theory) of a cream-colored, crystalline solid Elementary analysis: Cld: C 25.21 H 4.99 N 14.70 Br 47.91; Fnd: C 25.03 H 5.14 N 14.53 Br 47.65;

c) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-1,4,7,10-tetraazacyclododecane 20.72 g (180 mmol) of N-hydroxysuccinimide and 41.3 g (200 mmol) of dicyclohexylcarbodiimide are added to 67.16 g (89.94 mmol) of Gly-methyl-DOTA-tri-t.butylester (sodium bromide complex), dissolved in 500 ml of dimethylformamide, at 0° C., and it is stirred for 1 hour at this temperature. Then, it is stirred for 3 hours at room temperature. 15 g (22.49 mmol) of the title compound of Example 15b and 30.4 g (300 mmol) of triethylamine are added to this solution. It is stirred for 24 hours at room temperature. The solution is evaporated to the dry state, and the residue is taken up in 500 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum; the residue is chromatographed on silica gel (mobile solvent= dichloromethane/methanol=20:1).

Yield: 38.96 g (78% of theory) of a colorless, viscous oil Elementary analysis: Cld: C 57.87 H 8.80 N 13.88; Fnd: C 57.65 H 8.97 N 13.64;

d) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-(N-hexadecanoyl)-1,4,7,10-tetraazacyclododecane 20.74 g (9.34 mmol) of the title compound of Example 15c and 4.28 g (16.68 mmol) of palmitic acid are dissolved in 150 ml of dimethylformamide, and 7.42 g (30 mnol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=20:1)

Yield: 21.13 g (92% of theory) of a colorless, viscous oil Analysis: Cld: C 60.07 H 9.18 N 12.53; Fnd: C 60.10 H 9.35 N 12.37;

e) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd-complex}-10-(N-hexadecanoyl)-1,4,7,10-tetraazacyclododecane 10.33 g (4.2 mmol) of the title compound of Example 15d is dissolved in 200 ml of trifluoroacetic acid, and it is stirred for 12 hours at room temperature. It is evaporated to the dry state. The residue is dissolved in 100 ml of water and set at pH 3.3 with 50 aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.44 g (93% of theory) of a colorless, amorphous solid Water content: 10.2%; Elementary analysis (relative to anhydrous substance): Cld: C 43.23 H 5.96 N 12.75 Gd 19.52; Fnd: C 43.36 H 6.18 N 12.49 Gd 19.28; Relaxivity $R_1$ (l•mmol$^{-1}$s$^{-1}$) in plasma (20 MH$_z$,40° C.,0.47 Tesla):27.7

EXAMPLE 16 a) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-(N-pentadecanoyl)-1,4,7,10-tetraazacyclododecane 10.37 g (4.67 mmol) of the title compound of Example 15c and 2.26 g (9.33 mmol) of pentadecanoic acid are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=20:1)

Yield: 10.73 g (94% of theory) of a colorless, viscous oil Analysis: Cld: C 59.93 H 9.15 N 12.60; Fnd: C 59.71 H 9.34 N 12.43;

b) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-(N-pentadecanoyl)-1,4,7,10-tetraazacyclododecane 10.27 g (4.2 mmol) of the title compound of Example 16a is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.69 g (96% of theory) of a colorless, amorphous solid Water content: 11.4%; Elementary analysis (relative to anhydrous substance): Cld: C 42.99 H 5.91 N 12.82 Gd 19.63; Fnd: C 42.75 H 6.15 N 12.64 Gd 19.47;

EXAMPLE 17 a) 3-Oxa-hexadecanoic acid-t.butylester 10.51 g (53.9 mmol) of bromoacetic acid-tert-butylester is added to a mixture of 4.32 g (21.55 mmol) of tridecan-1-ol and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichloromethane/acetone= 20:10:1).

Yield: 5.29 g (78% of theory) of a colorless, viscous oil Elementary analysis: Cld: C 72.56 H 12.18; Fnd: C 72.34 H 12.39;

b) 3-Oxa-hexadecanoic acid 30 g (95.39 mmol) of the title compound of Example 17a is dissolved in 300 ml of trifluoroacetic acid, and it is stirred for 6 hours at room temperature. It is evaporated to the dry state. The residue is crystallized from hexane/ether.

Yield: 22.92 g (93% of theory) of a colorless solid. Elementary analysis: Cld: C 69.72 H 11.70; Fnd: C 69.57 H 11.84;

c) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-(N-3-oxa-hexadecanoyl)-1,4,7,10-tetraazacyclododecane 10.37 g (4.67 mmol) of the title compound of Example 15c and 2.41 g (9.33 mmol) of the title compound of Example 17b are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=20:1)

Yield: 10.57 g (92% of theory) of a colorless, viscous oil Analysis: Cld: C 59.94 H 9.09 N 12.52; Fnd: C 59.31 H 9.30 N 12.40;

d) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-(N-3-oxa-hexadecanoyl)-1,4,7,10-tetraazacyclododecane 10.34 g (4.2 mmol) of the title compound of Example 17c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.75 g (96% of theory) of a colorless, amorphous solid Water content: 11.0%; Elementary analysis (relative to anhydrous substance): Cld: C 42.70 H 5.88 N 12.74 Gd 19.50; Fnd: C 42.54 H 5.99 N 12.61 Gd 19.32;

EXAMPLE 18 a) 1,4,7-Tris{1,4,7-tris((N-t.butyloxycarbonylmethyl)-10-[N-(4,7-diaza-3,6,9-trioxo-nonane-2,9-diyl)]-1,4,7,10-tetraazacyclododecane}-10-(N-tetradecanoyl)-1,4,7,10-tetraazacyclododecane 10.37 g (4.67 mmol) of the title compound of Example 15c and 2.13 g (9.33 mmol) of tetradecanoic acid are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=20:1)

Yield: 10.79 g (95% of theory) of a colorless, viscous oil Analysis: Cld: C 59.78 H 9.12 N 12.67; Fnd: C 59.65 H 9.30 N 12.44;

b) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-(N-tetradecanoyl)-1,4,7,10-tetraazacyclododecane 10.21 g (4.2 mmol) of the title compound of Example 18a is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 50% aqueous sodium hydroxide solution, and the solution is dialyzed in an ultrafiltration cell (Amicon® YM-1), 6 passes.

The contents of the ultrafiltration cell are freeze-dried.

Yield: 9.73 g (97% of theory) of a colorless, amorphous solid Water content: 9.6%; Elementary analysis (relative to anhydrous substance): Cld: C 42.74 H 5.86 N 12.90 Gd 19.75; Fnd: C 42.55 H 5.99 N 12.68 Gd 19.54; Relaxivity $R_1$ (l•mmol$^{-1}$s$^{-1}$) in plasma (20 MH$_z$,40° C.,0.47 Tesla):24.3

EXAMPLE 19 a) 2-Amino-heptadecanoic acid

A cold, saturated solution of 29.42 g (0.55 mol) of ammonium chloride, 100 ml of concentrated ammonia solution and a solution of 26.95 g (0.55 mol) of sodium cyanide in 50 ml of water are added to a pressure cylinder. Then, it is cooled in ice water, and 48.1 g (0.2 mol) of hexadecanaldehyde, dissolved in 100 ml of isopropanol, is added. The pressure cylinder is sealed and stirred overnight at 80° C. It is evaporated to the dry state in a vacuum, the residue is taken up, and 100 ml of ethanol is taken up in 300 ml of hydrochloric acid and refluxed for 8 hours. It is evaporated to the dry state in a vacuum, the residue is extracted 3 times with 200 ml of ethanol each, and the filtrates are combined. It is evaporated to the dry state, and the residue is chromatographed on RP-18 (mobile solvent: graduated from acetonitrile/tetrahydrofuran/water).

Yield: 21.7 g (38% of theory) of a colorless solid Elementary analysis: Cld: C 71.53 H 12.36 N 4.91; Fnd: C 71.30 H 12.51 N 4.81;

b) 2-Benzyloxycarbonylamino-heptadecanoic acid 6.82 g (40 mmol) of benzyl chloroformate (Z—Cl) is added in drops to 10 g (35.03 mmol) of the title compound of Example 19a and 8.86 g (87.57 mmol) of triethylamine in 200 ml of tetrahydrofuran at 0° C. It is stirred for 5 hours at 0° C. It is evaporated to the dry state in a vacuum, the residue is taken up in 300 ml of dichloromethane and washed twice with 200 ml of 5% aqueous hydrochloric acid each. The organic phase is dried on magnesium sulfate and evaporated to the dry state. The residue is recrystallized from diisopropyl ether.

Yield: 11.02 g (75% of theory) of a colorless, crystalline solid Analysis: Cld: C 71.56 H 9.85 N 3.34; Fnd: C 71.43 H 10.04 N 3.25;

c) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-[N-(2-benzyloxycarbonylamino)-heptadecanoyl]-1,4,7,10-tetraazacyclododecane 10.37 g (4.67 mmol) of the title compound of Example 15c and 3.91 g (9.33 mmol) of the title compound of Example 19b are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=20:1)

Yield: 11.63 g (95% of theory) of a colorless, viscous oil Analysis: Cld: C 60.46 H 8.96 N 12.28; Fnd: C 60.25 H 8.92 N 12.05;

d) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-(N-2-aminoheptadecanoyl)-1,4,7,10-tetraazacyclododecane 11.5 g (4.39 mmol) of the title compound of Example 19c is dissolved in 300 ml of 2-propanol and 3 g of palladium catalyst (10% Pd/C) is added. It is hydrogenated for 6 hours at room temperature. The catalyst is filtered off, and the filtrate is evaporated to the dry state in a vacuum.

Yield: 10.91 g (quantitative) of a colorless, viscous oil Elementary analysis: Cld: C 59.85 H 9.19 N 12.95; Fnd: C 59.75 H 9.31 N 12.74;

e) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-{N-heptadecanoyl-2-amino-1,4,7-tris(N-t.butyloxycarbonylmethyl)-10-[N-(1-methyl-3-aza-2,5-dioxo-pentane-1,5-diyl)]-1,4,7,10-tetraazacyclododecane>}-1,4,7,10-tetraazacyclododecane 1.84 g (16 mmol) of N-hydroxysuccinimide and 2.48 g (12 mmol) of dicyclohexylcarbodiimide are added to 5.97 g (8 mmol) of Gly-methyl-DOTA-tri-t.butylester (sodium bromide complex), dissolved in 100 ml of dimethylformamide, at 0° C., and it is stirred for 1 hour at this temperature. Then, it is stirred for 3 hours at room temperature. 10 g (4.02 mmol) of the title compound of Example 19d and 2 g (20 mmol) of triethylamine are added to this solution. It is stirred for 24 hours at room temperature. The solution is evaporated to the dry state, and the residue is taken up in 300 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum. The residue is chromatographed on silica gel (mobile solvent= dichloromethane/methanol=20:1).

Yield: 12.29 g (94% of theory) of a colorless, viscous oil Elementary analysis: Cld: C 59.78 H 9.13 N 12.59; Fnd: C 59.61 H 9.31 N 12.38;

f) 1,4,7-Tris{1,4,7-tris(N-carboxylato)-10-[N-(4,7-diaza-3,6,9-trioxo-nonane-2,9-diyl)]-1,4,7,10-tetrazacyclododecane, Gd complex}-10-{N-heptadecanoyl-2-amino-<1,4,7-tris(N-carboxylatomethyl-10-[N-(1-methyl-3-aza-2,5-dioxo-pentane-1,5-diyl)]-1,4,7,10-tetraazacyclododecane, Gd complex>}-1,4,7,10-tetraazacyclododecane 10 g (3.21 mmol) of the title compound of Example 19e is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.33 g (6.42 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.42 g (96% of theory) of a colorless, amorphous solid Water content: 9.2%; Elementary analysis (relative to anhydrous substance): Cld: C 42.03 H 5.74 N 12.83 Gd 20.57; Fnd: C 42.19 H 5.61 N 12.64 Gd 20.38;

EXAMPLE 20 a) 1,4,7-Tris[N-(2-benzyloxycarbonylamino)-acetyl]-10-[N-(2-benzyloxy-carbonylamino)-heptadecanoyl]-1,4,7,10-tetraazacyclododecane 20 g (26.82 mmol) of the title compound of Example 15a and 16.78 g (40 mmol) of the title compound of Example 19b are dissolved in 150 ml of dimethylformamide, and 17.3 g (70 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 26.16 g (85% of theory) of a colorless, viscous oil
Analysis: Cld: C 65.95 H 7.55 N 9.77; Fnd: C 65.78 H 7.73 N 9.52;

b) 1,4,7-Tris[N-(2-amino)-acetyl]-10-[N-2-aminoheptadecanoyl]-1,4,7,10-tetraazacyclododecane, tetrahydrobromide 20 g (17.43 mmol) of the title compound of Example 20a is dissolved in 100 ml of acetic acid and added in drops to a 60° C. solution that consists of 300 ml of hydrogen bromide in glacial acetic acid (33%). It is stirred for 1 hour at 60° C. It is cooled to 0° C., and 2000 ml of diethyl ether is slowly added in drops while being stirred. The deposited precipitate is filtered out, rewashed twice with 200 ml of ether and dried in a vacuum furnace (60° C.).

Yield: 15.8 g (97 of theory) of colorless, crystalline solid
Elementary analysis: Cld: C 39.84 H 7.12 N 11.99 Br 34.20; Fnd: C 39.65 H 7.29 N 11.84 Br 34.06;

c) 1,4,7-Tris{N-[3,9-bis(N-t.butyloxycarbonylmethyl)-6-(N-3-aza-1,4-dioxo-pentane-1,5-diyl)-3,6,9-triazaundecanedioic acid-di-t.butylester]}-10-<N-heptadecanoyl-2-amino-[3,9-bis(N-t.butyloxycarbonylmethyl)-6-(N-3-aza-1,4-dioxo-pentane-1,5-diyl)-3,6,9-triazaundecanedioic acid-di-t.butylester]>-1,4,7,10-tetraazacyclododecane 9.21 g (80 mmol) of N-hydroxysuccinimide and 12.38 g (60 mmol) of dicyclohexyl carbodiimide are added to 24.79 g (40.2 mmol) of sym.-DTPA-tetra-t.butylester, dissolved in 300 ml of dimethylformamide, at 0° C., and it is stirred for 1 hour at this temperature. Then, it is stirred for 3 hours at room temperature. 3.76 g (4.02 mmol) of the title compound of Example 20b and 5.06 g (50 mmol) of triethylamine are added to this solution. It is stirred for 24 hours at room temperature. The solution is evaporated to the dry state, and the residue is taken up in 300 ml of dichloromethane. Dicyclohexylurea is filtered out, and the filtrate is washed twice with 200 ml of 5% aqueous sodium carbonate solution. The organic phase is dried on magnesium sulfate and evaporated to the dry state in a vacuum. The residue is chromatographed on silica gel (mobile solvent=dichloromethane/ethanol=30:1).

Yield: 10.77 g (89% of theory) of a colorless, viscous oil
Elementary analysis: Cld: C 60.26 H 9.18 N 9.31; Fnd: C 60.05 H 9.37 N 9.15;

d) 1,4,7-Tris{N-[3,9-bis(N-carboxylatomethyl)-6-(N-3-aza-1,4-dioxo-pentane-1,5-(diyl)-3,6,9-triazaundecane-1-carboxylato-11-acid, Gd complex, monosodium salt]}-10-<N-heptadecanoyl-2-amino-[3,9-bis(N-carboxylatomethyl)-6-(N-3-aza-1,4-dioxo-pentane-1,5-diyl)-3,6,9-triazaundecane-1-carboxylato-11-acid, Gd complex, monosodium salt]>1,4,7,10-tetraazacyclododecane 9.66 g (3.21 mmol) of the title compound of Example 20c is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.33 g (6.42 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). Dialysis is performed until the eluate has reached a conductivity of 10 µS. Then, the contents of the ultrafiltration cell are freeze-dried.

Yield: 8.68 g (96% of theory) of a colorless, amorphous powder Water content: 10.5%; Analysis (relative to anhydrous substance): Cld: C 37.09 H 4.65 N 9.94 Gd 22.33 Na 3.26; Fnd: C 36.91 H 4.82 N 9.75 Gd 22.18 Na 3.01;

EXAMPLE 21 a) 1,4,7-Tris[N-succinoyl-(3-benzyloxycarbonylamino-4-benzylester)]-1,4,7,10-tetraazacyclododecane 34.23 g (95.78 mmol) of N-(benzyloxycarbonyl)-asparaginic acid-benzyl ester and 5 g (29.02 mmol) of 1,4,7,10-tetraazacyclododecane (=cyclene) are dissolved in 200 ml of dimethylformamide, and 29.68 g (120 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: chloroform/methanol=30:1)

Yield: 13.47 g (39% of theory) of a colorless solid
Elementary analysis: Cld: C 65.59 H 6.01 N 8.24; Fnd: C 65.41 H 6.18 N 8.13;

b) 1,4,7-Tris[N-succinoyl-(3-benzyloxycarbonylamino-4-benzylester)]-10-[N-hexadecanoyl]-1,4,7,10-tetraazacyclododecane 13 g (10.92 mmol) of the title compound of Example 21a and 4.10 g (16 mmol) of palmitic acid are dissolved in 100 ml of dimethylformamide, and 6.18 g (25 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 14.53 g (93% of theory) of a colorless, viscous oil
Analysis: Cld: C 68.00 H 7.26 N 6.85; Fnd: C 67.85 H 7.41 N 6.66;

c) 1,4,7-Tris[N-(3-amino)-succinic acid-semi-amide]-10-(N-hexadecanoyl)-1,4,7,10-tetraazacyclododecane 14.3 g (10 mmol) of the title compound of Example 21b is dissolved in 300 ml of methanol and 30 ml of water, and 3 g of palladium catalyst (10% Pd/C) is added. It is hydrogenated for 6 hours at room temperature. The catalyst is filtered off, and the filtrate is evaporated to the dry state in a vacuum.

Yield: 7.55 g (quantitative) of a colorless solid. Elementary analysis: Cld: C 57.20 H 8.67 N 12.97; Fnd: C 57.03 H 8.78 N 12.84;

d) 1,4,7-Tris{1,4,7-tris(N-t.butyloxycarbonylmethyl)-10-[N-(4,7-diaza-3,6,10-trioxo-8-carboxy-decane-2,10-diyl)]-1,4,7,10-tetraazacyclododecane}-10-(N-hexadecanoyl)-1,4,7,10-tetraazacyclododecane 11.51 g (100 mmol) of N-hydroxysuccinimide and 16.51 g (80 mmol) of dicyclohexylcarbodiimide are added to 55.26 g (74 mmol) of Gly-methyl-DOTA-tri-t.butylester (sodium bromide complex), dissolved in 300 ml of dimethylformamide, at 0° C., and it is stirred for 1 hour at this temperature. Then, it is stirred for 3 hours at room temperature. 7 g (9.26 mmol) of the title compound of Example 21c and 10.12 g (100 mmol) of triethylamine are added to this solution. It is stirred for 24 hours at room temperature. The solution is evaporated to the dry state in a vacuum, and the residue is taken up in 500 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum. The residue is chromatographed on silica gel (mobile solvent: dichloromethane/methanol=10:1; +1% acetic acid).

Yield: 21.21 g (87% of theory) of a colorless solid
Elementary analysis: Cld: C 58.84 H 8.80 N 11.70; Fnd: C 58.65 H 8.97 N 11.53;

e) 1,4,7-Tris{1,4,7-tris(N-carboxylatomethyl)-10-[N-(4,7-diaza-3,6,10-trioxo-8-carboxy-decane-2,10-diyl)]-1,4,7,10- tetraazacyclododecane, Gd complex, monosodium salt}-10-(N-hexadecanoyl)-1,4,7,10-tetraazacyclododecane 11.06 g (4.2 mmol) of the title compound of Example 21d is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.2 with 5% aqueous sodium hydroxide solution, and the solution is dialyzed in an ultrafiltration cell (Amicon® YM-1). The contents of the ultrafiltration cell are freeze-dried.

Yield: 10.5 g (94% of theory) of a colorless, amorphous solid Water content: 10.5%; Analysis (relative to anhydrous substance): Cld: C 41.99 H 5.65 N 11.58 Gd 17.73 Na 2.59; Fnd: C 41.71 H 5.81 N 11.37 Gd 17.51 Na 2.32;

EXAMPLE 22 a) 1,4,7-Tris[N-succinoyl-(3-benzyloxycarbonylamino-4-benzylester)]-10-[N-(3-oxa-hexadecanoyl)]-1,4,7,10-tetraazacyclododecane 13 g (10.92 mmol) of the title compound of Example 21a and 4.13 g (16 mmol) of the title compound of Example 17b are dissolved in 100 ml of dimethylformamide, and 6.18 g (25 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 14.69 g (95% of theory) of a colorless, viscous oil Analysis: Cld: C 67.82 H 7.19 N 6.92; Fnd: C 67.64 H 7.34 N 6.71;

b) 1,4,7-Tris[N-(3-amino)-succinic acid-semi-amide]-10-[N-(3-oxa)-hexadecanoyl]-1,4,7,10-tetraazacyclododecane 14.5 g (10.23 mmol) of the title compound of Example 22a is dissolved in 300 ml of methanol and 30 ml of water, and 3 g of palladium catalyst (10% Pd/C) is added. It is hydrogenated for 6 hours at room temperature. The catalyst is filtered off, and the filtrate is evaporated to the dry state in a vacuum.

Yield: 7.76 g (quantitative) of a colorless solid Elementary analysis: Cld: C 55.47 H 8.38 N 12.94; Fnd: C 55.31 H 8.49 N 12.75;

c) 1,4,7-Tris{1,4,7-tris(N-t.butyloxycarbonylmethyl)-10-[N-(4,7-diaza-3,6,10-trioxo-8-carboxy-decane-2,10-diyl)]-1,4,7,10-tetraazacyclododecane}-10-[N-(3-oxa)-hexadecanoyl]-1,4,7,10-tetraazacyclododecane 11.51 g (100 mmol) of N-hydroxysuccinimide and 16.51 g (80 mmol) of dicyclohexylcarbodiimide are added to 55.26 g (74 mmol) of Gly-methyl-DOTA-tri-t.butylester (sodium bromide complex), dissolved in 300 ml of dimethylformamide, at 0° C., and it is stirred for 1 hour at this temperature. Then, it is stirred for 3 hours at room temperature. 7.02 g (9.26 mmol) of the title compound of Example 22a and 10.12 g (100 mmol) of triethylamine are added to this solution. It is stirred for 24 hours at room temperature. The solution is evaporated to the dry state, and the residue is taken up in 500 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum. The residue is chromatographed on silica gel (mobile solvent: chloroform/methanol=15:1).

Yield: 22.2 g (91% of theory) of a colorless solid Elementary analysis: Cld: C 58.34 H 8.72 N 11.69; Fnd: C 58.23 H 8.89 N 11.60;

d) 1,4,7-Tris{1,4,7-tris(N-carboxylatomethyl)-10-[N-(4,7-diaza-3,6,10-trioxo-8-carboxy-decane-2,10-diyl)]-1,4,7,10-tetraazacyclododecane, Gd complex, monosodium salt}-10-(N-(3-oxa)-hexadecanoyl]-1,4,7,10-tetraazacyclododecane 11.07 g (4.2 mmol) of the title compound of Example 22c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.2 with 5% aqueous sodium hydroxide solution, and the solution is dialyzed in an ultrafiltration cell (Amicon® YM-1). The contents of the ultrafiltration cell are freeze-dried.

Yield: 10.62 g (95% of theory) of a colorless, amorphous solid Water content: 7.8%; Analysis (relative to anhydrous substance): Cld: C 41.51 H 5.57 N 11.58 Gd 17.72 Na 2.59; Fnd: C 41.35 H 5.72 N 11.39 Gd 17.52 Na 2.33;

EXAMPLE 23 a) 1,4,7-Tris[N-succinoyl-(3-benzyloxycarbonylamino-4-benzylester)]-10-(N-tetradecanoyl)-1,4,7,10-tetraazacyclododecane 13 g (10.92 mmol) of the title compound of Example 21a and 3.65 g (16 mmol) of tetradecanoic acid are dissolved in 100 ml of dimethylformamide, and 6.18 g (25 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 14.24 g (93% of theory) of a colorless, viscous oil Analysis: Cld: C 67.65 H 7.11 N 6.99; Fnd: C 67.48 H 7.29 N 6.78;

b) 1,4,7-Tris[N-(3-amino)-succinic acid-semi-amide]-10-(N-tetradecanoyl)-1,4,7,10-tetraazacyclododecane 14 g (9.98 mmol) of the title compound of Example 23a is dissolved in 300 ml of methanol and 30 ml of water, and 3 g of palladium catalyst (10% Pd/C) is added. It is hydrogenated for 6 hours at room temperature. The catalyst is filtered off, and the filtrate is evaporated to the dry state in a vacuum.

Yield: 7.26 g (quantitative) of a colorless, viscous oil Elementary analysis: Cld: C 56.10 H 8.45 N 13.47; Fnd: C 56.03 H 8.63 N 13.30;

c) 1,4,7-Tris{1,4,7-tris(N-t.butyloxycarbonylmethyl)-10-[N-(4,7-diaza-3,6,10-trioxo-8-carboxy-decane-2,10-diyl)]-1,4,7,10-tetraazacyclododecane}-10-(N-tetradecanoyl)-1,4,7,10-tetraazacyclododecane 11.51 g (100 mmol) of N-hydroxysuccinimide and 16.51 g (80 mmol) of dicyclohexylcarbodiimide are added to 55.26 g (74 mmol) of Gly-methyl-DOTA-t.butylester (sodium bromide complex), dissolved in 300 ml of dimethylformamide, at 0° C., and it is stirred for 1 hour at this temperature. Then, it is stirred for 3 hours at room temperature. 6.74 g (9.26 mmol) of the title compound of Example 23b and 10.12 g (100 mmol) of triethylamine are added to this solution. It is stirred for 24 hours at room temperature. The solution is evaporated to the dry state, and the residue is taken up in 500 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum. The residue is chromatographed on silica gel (mobile solvent=chloroform/methanol=15:1).

Yield: 21.95 g (91% of theory) of a colorless solid Elementary analysis: Cld: C 58.55 H 8.74 N 11.83; Fnd: C 58.35 H 8.91 N 11.66;

d) 1,4,7-Tris{1,4,7-tris(N-carboxylatomethyl)-10-[N-(4,7-diaza-3,6,10-trioxo-8-carboxy-decane-2,10-diyl)]-1,4,7,10-tetraazacyclododecane, Gd complex, monosodium salt}-10-(N-tetradecanoyl]-1,4,7,10-tetraazacyclododecane 10.94 g (4.2 mmol) of the title compound of Example 23c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.2 with 5% aqueous sodium hydroxide solution, and the solution is dialyzed in an ultrafiltration cell (Amicon® YM-1). The contents of the ultrafiltration cell are freeze-dried.

Yield: 10.72 g (97% of theory) of a colorless, amorphous solid Water content: 11.2%; Elementary analysis (relative to anhydrous substance): Cld: C 41.53 H 5.55 N 11.71 Gd 17.92 Na 2.62; Fnd: C 41.41 H 5.72 N 11.55 Gd 17.74 Na 2.41;

EXAMPLE 24 a) 1,4,7,10-Tetrakis[3,9-bis(N-t.butyloxycarbonylmethyl)-3,6,9-triaza-undecane-1,11-dicarboxylic acid-di-t.butylester-6-(2-oxo-methyl)]-1,4,7,10,13-pentaazacyclopentadecane 46.25 g (75 mmol) of sym.-DTPA-tetra-t.butylester and 2 g (9.29 mmol) of 1,4,7,10,13-pentaazacyclopentadecane are dissolved in 300 ml of dimethylformamide, and 37.1 g (150 mmol) of 2-ethoxy-1-ethoxycarbonyl-1,2-dihydroquinoline is added at 0° C. It is stirred for 24 hours at room temperature. 1000 ml of water is added and extracted twice with 300 ml of chloroform each. The organic phase is dried on magnesium sulfate. It is evaporated to the dry state in a vacuum, and the residue is chromatographed on silica gel (mobile solvent: methylene chloride/methanol=25:1)

Yield: 17.97 g (74% of theory) of a colorless, viscous oil Elementary analysis: Cld: C 59.72 H 9.14 N 9.11; Fnd: C 59.51 H 9.32 N 8.95;

b) 1,4,7,10-Tetrakis[3,9-bis(N-t.butyloxycarbonylmethyl)-3,6,9-triaza-undecane-1,11-dicarboxylic acid-di-t.butylester-6-(2-oxo-methyl)]-13-<N-[4-(11-oxaundecyl)]-benzoyl>-1,4,7,10,13-pentaazacyclopentadecane 17 g (6.50 mmol) of the title compound of Example 24a and 3.06 g (11 mmol) of the title compound of Example 8a are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 17.19 g (92% of theory) of a colorless, viscous oil Analysis: Cld: C 61.42 H 9.15 N 8.28; Fnd: C 61.27 H 9.30 N 8.05;

c) 1,4,7,10-Tetrakis{[3,9-bis(N-carboxylatomethyl)-3,6,9-triaza-undecane-1-carboxylato-11-acid-6-(2-oxo-methyl)]-Gd complex, sodium salt}-13-<N-(4-(11-oxaundecyl)-benzoyl>-1,4,7,10,13-pentaazacyclopentadecane 10 g (3.48 mmol) of the title compound of Example 24b is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.52 g (6.96 mmol) of gadolinium oxide is added, and it is stirred for 2 hours at 70° C. It is cooled to room temperature and set at pH 7.2 with 10% aqueous sodium hydroxide solution. The solution is mixed with 3 g of activated carbon, cooled for 1 hour at room temperature and filtered. The filtrate is loaded into an ultrafiltration cell and dialyzed (Amicon® YM-1). It is dialyzed until the eluate has reached a conductivity of 10 µS. Then, the contents of the ultrafiltration cell are freeze-dried.

Yield: 9.05 g (97% of theory) of a colorless, amorphous powder Water content: 9.6%; Analysis (relative to anhydrous substance): Cld: C 37.17 H 4.40 N 8.88 Gd 23.45 Na 3.43; Fnd: C 36.94 H 4.60 N 8.71 Gd 23.23 Na 3.17;

EXAMPLE 25 a) 1,4,7,10,13-Pentakis{1,4,7-tris(N-t.butyloxycarbonylmethyl)-10-[N-(4-aza-3,6-dioxo-hexane-2,6-diyl)]-1,4,7,10-tetraazacyclododecane}-1,4,7,13,16-hexaazacyclooctadecane 47.5 g (77 mmol) of sym.-DTPA-tetra-t.butylester and 2 g (7.74 mmol) of 1,4,7,10,13,16-hexaazacyclooctadecane are dissolved in 300 ml of dimethylformamide, and 37.1 g (150 mmol) of 2-ethoxy-1-ethoxycarbonyl-1,2-dihydroquinoline is added at 0° C. It is stirred for 24 hours at room temperature. 1000 ml of water is added and extracted twice with 300 ml of chloroform each. The organic phase is dried on magnesium sulfate. It is evaporated to the dry state in a vacuum, and the residue is chromatographed on silica gel (mobile solvent: methylene chloride/methanol= 25:1)

Yield: 18.61 g (71% of theory) of a colorless, viscous oil Elementary analysis: Cld: C 59.21 H 9.08 N 12.82; Fnd: C 59.01 H 9.24 N 12.71;

b) 1,4,7,10,13-Pentakis{1,4,7-tris(N-t.butyloxycarbonylmethyl)-10-[N-(4-aza-3,6-dioxo-hexane-2,6-diyl)]-1,4,7,10-tetraazacyclododecane}-16-(N-hexadecanoyl)-1,4,7,13,16-hexaaza-cyclooctadecane 18 g (5.31 mmol) of the title compound of Example 25a and 2.31 g (9 mmol) of palmitic acid are dissolved in 100 ml of dimethylformamide, and 4.2 g (17 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1).

Yield: 18.29 g (95% of theory) of a colorless, viscous oil Analysis: Cld: C 60.62 H 9.31 N 11.98; Fnd: C 60.47 H 9.48 N 11.75;

c) 1,4,7,10,13-Pentakis{1,4,7-tris(N-carboxylatomethyl)-10-[N-(4-aza-3,6-dioxo-hexane-2,6-diyl)]-1,4,7,10-tetraazacyclododecane, Gd complex}-16-(N-hexadecanoyl)-1,4,7,13,16-hexaaza-cyclooctadecane 12.61 g (3.48 mmol) of the title compound of Example 25b is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 3.15 g (8.7 mmol) of gadolinium oxide is added, and it is stirred for 3 hours at 90° C. It is allowed to reach room temperature, set at pH 7.2 with 5% aqueous sodium hydroxide solution, and the solution is dialyzed in an ultrafiltration cell (Amicon® YM-1). The contents of the ultrafiltration cell are freeze-dried.

Yield: 12.21 g (96% of theory) of a colorless, amorphous solid Water content: 10.2%; Elementary analysis (relative to anhydrous substance): Cld: C 40.43 H 5.52 N 11.88 Gd 21.52 Na 3.15; Fnd: C 40.21 H 5.75 N 11.67 Gd 21.35 Na 2.84;

EXAMPLE 26 a) 3-Oxa-tridecan-1-ol 44.88 g (800 mmol) of fine powdered potassium hydroxide is added to 32.93 g (200 mmol) of the tetrahydropyranyl ether of 2-chloroethanol, 1 g (3.6 mmol) of tetrabutylammonium chloride and 20 g (126.36 mmol) of decan-1-ol in 300 ml of toluene, and it is refluxed for 24 hours. Solid is filtered out, and the filtrate is evaporated to the dry state. 500 ml of ethanol/50 ml of 10% aqueous hydrochloric acid are added to the residue (oil) that is thus obtained, and it is stirred for one hour at room temperature. It is evaporated to the dry state in a vacuum, and the residue is chromatographed on silica gel (mobile solvent: hexane/acetone=20:1).

Yield; 21.73 g (85% of theory) of a colorless oil Elementary analysis: Cld: C 71.23 H 12.95; Fnd: C 71.05 H 13.10;

b) 3,6-Dioxa-hexadecanoic acid-t.butylester 10.51 g (53.9 mmol) of bromoacetic acid-tert-butyl ester is added to a mixture of 4.36 g (21.55 mmol) of the title compound of Example 26a and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichloromethane/acetone=20:10:1).

Yield: 6.34 g (93% of theory) of a colorless, viscous oil Elementary analysis: Cld: C 68.31 H 11.46; Fnd: C 68.15 H 11.28;

c) 3,6-Dioxa-hexadecanoic acid 6.2 g (19.59 mmol) of the title compound of Example 26b is dissolved in 100 ml of trifluoroacetic acid, and it is stirred for 6 hours at room temperature. It is evaporated to the dry state. The residue is crystallized from hexane/ether.

Yield: 4.69 g (92% of theory) of a colorless solid Elementary analysis (relative to anhydrous substance): Cld: C 64.58 H 10.84; Fnd: C 64.37 H 11.15;

d) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-[N-(3,6-dioxa-hexanoyl)]-1,4,7,10-tetraazacyclododecane 20.74 g (9.34 mmol) of the title compound of Example 15c and 3.65 g (14 mmol) of the title compound of Example 26c are dissolved in 150 ml of dimethylformamide, and 7.42 g (30 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=20:1)

Yield: 20.02 g (87% of theory) of a colorless, viscous oil Analysis: Cld: C 59.00 H 9.00 N 12.51; Fnd: C 58.78 H 9.17 N 12.35;

e) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-[N-(3,6-dioxa-hexanoyl)]-1,4,7,10-tetraazacyclododecane 10.35 g (4.2 mmol) of the title compound of Example 26d is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.66 g (95% of theory) of a colorless, amorphous solid Water content: 11.1%; Elementary analysis (relative to anhydrous substance): Cld: C 42.17 H 5.79 N 12.73 Gd 19.49; Fnd: C 42.01 H 5.94 N 12.60 Gd 19.28;

EXAMPLE 27 a) 1,4,7-Tris[N-(2-benzyloxycarbonylamino-3-phenyl)-propionyl]-1,4,7,10-tetraazacyclododecane 35.66 g (89.96 mmol) of N-(benzyloxycarbonyl)-phenylalanine-N-hydroxysuccinimide ester and 10.12 g (100 mmol) of triethylamine are added to 5 g (29.02 mmol) of 1,4,7,10-tetraazacyclododecane (=cyclene) in 300 ml of toluene, and it is refluxed for 12 hours. It is evaporated to the dry state in a vacuum, the residue is taken up in 400 ml of dichloromethane, and the organic phase is washed twice with 5% aqueous sodium carbonate solution. The organic phase is dried on magnesium sulfate and evaporated to the dry state in a vacuum. The residue is chromatographed on silica gel (mobile solvent: ethyl acetate/ethanol=20:1).

Yield: 18.58 g (63 of theory) of a colorless foam Elementary analysis: Cld: C 69.73 H 6.45 N 9.65; Fnd: C 69.41 H 6.63 N 9.47;

b) 1,4,7-Tris[N-(2-benzyloxycarbonylamino-3-phenyl)-propionyl]-10-(N-heptanoyl)-1,4,7,10-tetraazacyclododecane 18 g (17.71 mmol) of the title compound of Example 27a and 3.25 g (25 mmol) of heptanoic acid are dissolved in 100 ml of dimethylformamide, and 9.89 g (40 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 18.19 g (91% of theory) of a colorless, viscous oil Analysis: Cld: C 70.25 H 6.88 N 8.69; Fnd: C 70.11 H 6.99 N 8.70;

c) 1,4,7-Tris[N-(2-amino-3-phenyl)-propionyl]-10-(N-heptanoyl)-1,4,7,10-tetraazacyclododecane, trihydrobromide 18 g (15.95 mmol) of the title compound of Example 27b is dissolved in 100 ml of acetic acid and added in drops to a 60° C. solution that consists of 300 ml of hydrogen bromide in glacial acetic acid (33%). It is stirred for 1 hour at 60° C. It is cooled to 0° C., and 2000 ml of diethyl ether is slowly added in drops while being stirred. The deposited precipitate is filtered, rewashed twice with 200 ml of ether and dried in a vacuum furnace (60° C.).

Yield: 14.83 g (96 of theory) of a colorless, crystalline solid Elementary analysis: Cld: C 52.08 H 6.45 N 10.12 Br 24.75; Fnd: C 51.85 H 6.61 N 10.00 Br 24.48;

d) 1,4,7-Tris{N-[3-phenylpropionyl-2-amino-<N-(2-benzyl-3,6-diaza-7-oxo-8-yl-nonanoyl-8-yl-[1,4,7-tris(N-t.butyloxycarbonylmethyl)-1,4,7,10-tetraazacyclododecane-10-yl>]}10-(N-heptanoyl)-1,4,7,10-tetraazacyclododecane 11.51 g (100 mmol) of N-hydroxysuccinimide and 16.51 g (80 mmol) of dicyclohexylcarbodiimide are added to 55.26 g (74 mmol) of Gly-methyl-DOTA-tri-t.butylester (sodium bromide complex), dissolved in 300 ml of dimethylformamide, at 0° C., and it is stirred for one hour at this temperature. Then, it is stirred for 3 hours at room temperature. 8.97 g (9.26 mmol) of the title compound of Example 27c and 10.12 g (100 mmol) of triethylamine are added to this solution. It is stirred for 24 hours at room temperature. The solution is evaporated to the dry state, and the residue is taken up in 800 ml of dichloromethane. Dicyclohexylurea is filtered out, and the filtrate is washed twice with 300 ml of 5% aqueous sodium carbonate solution. The organic phase is dried on magnesium sulfate and evaporated to the dry state in a vacuum. The residue is chromatographed on silica gel (mobile solvent: dichloromethane/methanol=20:1).

Yield: 21.7 g (90% of theory) of a colorless, viscous oil
Elementary analysis: Cld: C 62.28 H 8.67 N 11.84; Fnd: C 62.09 H 8.84 N 11.69;

e) 1,4,7-Tris{N-[3-phenylpropionyl-2-amino-<N-(2-benzyl-3,6-diaza-7-oxo)-nonanoyl-8-Yl-[1,4,7-tris[N-carboxylatomethyl)-1,4,7,10-tetraazacyclododecan-10-yl]>]}-10-(N-heptanoyl)-1,4,7,10-tetraazacyclododecane 10.93 g (4.2 mmol) of the title compound of Example 27d is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 10.43 g (97% of theory) of a colorless, amorphous solid Water content: 12.0%; Elementary analysis (relative to anhydrous substance): Cld: C 46.43 H 5.63 N 12.03 Gd 18.42; Fnd: C 46.22 H 5.75 N 11.85 Gd 18.23; Relaxivity $R_1$ ($l \cdot mmol^{-1}s^{-1}$) in plasma (20 $MH_z$,40° C.,0.47 Tesla):12.8

EXAMPLE 28 a) 1,4,7-Tris{3,9-bis(N-t.butyloxycarbonylmethyl)-6-[N-(3-aza-2,5-dioxo)-pentane-1,5-diyl]-3,6,9-triazaundecanedioic acid-di-t.butylester}-10-(N-pentadecyl)-1,4,7,10-tetraazacyclododecane 150 ml of acetonitrile is added to 20 g (9.33 mmol) of the title compound of Example 1b, 6.91 g (50 mmol) of potassium carbonate and 5.07 g (15 mmol) of pentadecyl-1-iodide, and it is heated for 12 hours to 60° C. Solid is filtered out, the filtrate is evaporated to the dry state in a vacuum, and the residue is chromatographed on silica gel (mobile solvent: dichloromethane/2-propanol=20:1)

Yield: 17.78 g (81% of theory) of a colorless, viscous oil
Elementary analysis: Cld: C 60.74 H 9.34 N 9.52; Fnd: C 60.54 H 9.51 N 9.37;

b) 1,4,7-Tris{3,9-bis(N-carboxylatomethyl)-6-[N-(3-aza-2,5-dioxo)-pentane-1,5-diyl]-3,6,9-triazaundecane-1-carboxylato-11-acid, Gd complex}-disodium salt-10-[N-(pentadecyl)]-1,4,7,10-tetraazacyclododecane 9.88 g (4.2 mmol) of the title compound of Example 28a is dissolved in 200 ml of trifluoroacetic acid, and it is stirred for 12 hours at room temperature. It is evaporated to the dry state in a vacuum. The residue is dissolved in 100 ml of water and set at pH 4 with 10% aqueous sodium hydroxide solution. Then, 2.28 g (6.3 mmol) of gadolinium oxide is added, and it is stirred for 2 hours at 70° C. It is cooled to room temperature and set at pH 7.2 with 10% aqueous sodium hydroxide solution. The solution is mixed with 2 g of activated carbon, cooled for 1 hour at room temperature and filtered. The filtrate is loaded into an ultrafiltration cell and dialyzed (Amicon® YM-1). It is dialyzed until the eluate has reached a conductivity of 10 μS. Then, the contents of the ultrafiltration cell are freeze-dried.

Yield: 8.81 g (96% of theory) of a colorless, amorphous powder Water content: 7.6%; Analysis (relative to anhydrous substance): Cld: C 39.00 H 5.12 N 10.25 Gd 21.58 Na 2.10; Fnd: C 38.83 H 5.29 N 10.11 Gd 21.39 Na 1.87;

EXAMPLE 29 a) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-(N-tetradecyl)-1,4,7,10-tetraazacyclododecane 150 ml of acetonitrile is added to 20 g (9.33 mmol) of the title compound of Example 15c, 6.91 g (50 mmol) of potassium carbonate and 4.86 g (15 mmol) of tetradecyl-1-iodide, and it is heated for 12 hours to 60° C. Solid is filtered out, the filtrate is evaporated to the dry state in a vacuum, and the residue is chromatographed on silica gel (mobile solvent: dichloromethane/methanol=20:1)

Yield: 20.52 g (91% of theory) of a colorless, viscous oil
Elementary analysis: Cld: C 60.12 H 9.26 N 12.75; Fnd: C 59.87 H 9.48 N 12.55;

b) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-(N-tetradecyl)-1,4,7,10-tetraazacyclododecane 10.15 g (4.2 mmol) of the title compound of Example 29a is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.47 g (95% of theory) of a colorless, amorphous solid Water content: 11.5%; Elementary analysis (relative to anhydrous substance): Cld: C 42.99 H 5.98 N 12.98 Gd 19.86; Fnd: C 42.75 H 6.18 N 12.75 Gd 19.64;

EXAMPLE 30 a) 7,7-Diphenyl-hept-6-ene-carboxylic acid

A solution that consists of 10 g (54.9 mmol) of benzophenone and 25.10 g (54.9 mmol) of 6-(triphenylphosphonium)-hexanoic acid bromide, dissolved in 150 ml of dimethyl sulfoxide/150 ml of tetrahydrofuran, is added in drops to 13.54 g (120.7 mmol) of potassium-t.-butylate, dissolved in 35 ml of dimethyl sulfoxide/35 ml of tetrahydrofuran, at 0° C. It is stirred overnight at room temperature. The solution is added to 2 l of ice water and set at pH 2 with 20% aqueous hydrochloric acid. It is extracted three times with 200 ml of diethyl ether each. The combined organic phases are washed twice with 200 ml of saturated aqueous sodium chloride solution each, dried on magnesium sulfate and evaporated to the dry state in a vacuum. The residue is chromatographed on silica gel (mobile solvent: hexane/ethyl acetate=5:1/+1% acetic acid).

Yield: 12 g (78% of theory) of a colorless solid Elementary analysis: Cld: C 81.40 H 7.19; Fnd: C 81.17 H 7.38;

b) 7,7-Diphenylheptanoic acid 11.5 g (41 mmol) of the title compound of Example 30a is dissolved in 200 ml of 2-propanol, and 3 g of palladium catalyst (10% Pd/C) is added. It is hydrogenated for 6 hours at room temperature. The catalyst is filtered off, and the filtrate is evaporated to the dry state in a vacuum.

Yield: 11.58 g (quantitative) of a colorless solid. Elementary analysis: Cld: C 80.82 H 7.85; Fnd: C 80.65 H 7.99;

c) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-[N-(7,7-diphenylheptanoyl)]-1,4,7,10-tetraazacyclodedecane 2.63 g (9.33 mmol) of the title compound of Example 30b and 10.37 g (4.67 mmol) of the title compound of Example 15c are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=25:1)

Yield: 11.03 g (95% of theory) of a colorless, viscous oil
Analysis: Cld: C 60.90 H 8.68 N 12.40; Fnd: C 60.75 H 8.83 N 12.27;

d) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-[N-(7,7-diphenylheptanoyl)]-1,4,7,10-tetraazacyclododecane 10.44 g (4.2 mmol) of the title compound of Example 30c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1). The contents of the ultrafiltration cell are freeze-dried.

Yield: 9.85 g (96% of theory) of a colorless, amorphous solid Water content: 9.7%; Elementary analysis (relative to anhydrous substance): Cld: C 44.25 H 5.49 N 12.61 Gd 19.31; Fnd: C 44.09 H 5.72 N 12.40 Gd 19.13;

EXAMPLE 31 a) 7-(Biphen-4-yl)-hept-6-enoic acid

A solution that consists of 10 g (54.9 mmol) of 4-biphenylaldehyde and 25.10 g (54.9 mmol) of 6-(triphenylphosphonium)-hexanoic acid bromide, dissolved in 150 ml of dimethyl sulfoxide/150 ml of tetrahydrofuran, is added in drops to 13.54 g (120.7 mmol) of potassium-t.-butylate, dissolved in 35 ml of dimethyl sulfoxide/35 ml of tetrahydrofuran, at 0° C. It is stirred overnight at room temperature. The solution is added to 2 l of ice water and set at pH 2 with 20% aqueous hydrochloric acid. It is extracted 3 times with 200 ml of diethyl ether each. The combined organic phases are washed twice with 200 ml of saturated aqueous sodium chloride solution each, dried on magnesium sulfate and evaporated to the dry state in a vacuum. The residue is chromatographed on silica gel (mobile solvent: a-hexane/ethyl acetate=5:1/+1% acetic acid).

Yield: 12.47 g (81% of theory) of a colorless solid Elementary analysis: Cld: C 81.40 H 7.19; Fnd: C 81.28 H 7.31;

b) 7-(Biphen-4-yl)-heptanoic acid 12 g (42.8 mmol) of the title compound of Example 31a is dissolved in 200 ml of 2-propanol, and 3 g of palladium catalyst (10% Pd/C) is added. It is hydrogenated for 6 hours at room temperature. The catalyst is filtered off, and the filtrate is evaporated to the dry state in a vacuum.

Yield: 12.07 g (quantitative) of a colorless solid. Elementary analysis: Cld: C 80.82 H 7.85; Fnd: C 80.68 H 7.99;

c) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-[N-7-(biphen-4-yl-heptanoyl]-1,4,7,10-tetraazacyclododecane 2.63 g (9.33 mmol) of the title compound of Example 31b and 10.37 g (4.67 mmol) of the title compound of Example 15c are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=25:1)

Yield: 10.79 g (93% of theory) of a colorless, viscous oil Analysis: Cld: C 60.90 H 8.68 N 12.40; Fnd: C 60.57 H 8.89 N 12.18;

d) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd-complex}-10-[N-7-(biphen-4-yl-heptanoyl]-1,4,7,10-tetraazacyclododecane 10.44 g (4.2 mmol) of the title compound of Example 31c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.95 g (97% of theory) of a colorless, amorphous solid Water content: 8.4%; Elementary analysis (relative to anhydrous substance): Cld: C 44.25 H 5.49 N 12.61 Gd 19.31; Fnd: C 44.08 H 5.68 N 12.43 Gd 19.12;

EXAMPLE 32 a) 7-(2,3,4-Trihydronaphthalin-1-yl)-hept-6-enoic acid

A solution that consists of 8.03 g (54.9 mmol) of α-tetralone and 25.10 g (54.9 mmol) of 6-(triphenylphosphonium)-hexanoic acid bromide, dissolved in 150 ml of dimethyl sulfoxide/150 ml of tetrahydrofuran, is added in drops to 13.54 g (120.7 mmol) of potassium-t.-butylate, dissolved in 35 ml of dimethyl sulfoxide/35 ml of tetrahydrofuran, at 0° C. It is stirred overnight at room temperature. The solution is added to 2 l of ice water and set at pH 2 with 20% aqueous hydrochloric acid. It is extracted 3 times with 200 ml of diethyl ether each. The combined organic phases are washed twice with 200 ml of saturated aqueous sodium chloride solution each, dried on magnesium sulfate and evaporated to the dry state in a vacuum. The residue is chromatographed on silica gel (mobile solvent: hexane/ethyl acetate=5:1/+1% acetic acid).

Yield: 10.33 g (77% of theory) of a colorless solid Elementary analysis: Cld: C 78.65 H 8.25; Fnd: C 78.49 H 8.37;

b) 7-(1,2,3,4-Tetrahydronaphthalin-1-yl)-heptanoic acid 10 g (40.93 mmol) of the title compound of Example 32a is dissolved in 200 ml of 2-propanol, and 3 g of palladium catalyst (10% Pd/C) is added. It is hydrogenated for 6 hours at room temperature. The catalyst is filtered off, and the filtrate is evaporated to the dry state in a vacuum.

Yield: 10.08 g (quantitative) of a colorless, viscous oil Elementary analysis: Cld: C 78.01 H 9.00; Fnd: C 77.88 H 9.19;

c) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-<N-[7-(1,2,3,4-tetrahydronaphthalin-1-yl)-heptanoyl]>-1,4,7,10-tetraazacyclododecane 2.29 g (9.33 mmol) of the title compound of Example 32b and 10.37 g (4.67 mmol) of the title compound of Example 15c are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=25:1)

Yield: 10.75 g (94% of theory) of a colorless, viscous oil Analysis: Cld: C 60.32 H 8.81 N 12.58; Fnd: C 60.17 H 8.95 N 12.39;

d) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-<N-[7-(1,2,3,4-tetrahydronaphthalin-1-yl)-heptanoyl]>-1,4,7,10-tetraazacyclododecane 10.29 g (4.2 mmol) of the title compound of Example 32c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.81 g (97% of theory) of a colorless, amorphous powder Water content: 10.4%; Elementary analysis (relative to anhydrous substance): Cld: C 43.42 H 5.57 N 12.80 Gd 19.60; Fnd: C 43.26 H 5.73 N 12.61 Gd 19.42;

EXAMPLE 33 a) 3-(4,4-Diphenylcyclohexyl)-3-oxapropionic acid-t.butylester 10.51 g (53.9 mmol) of bromoacetic acid-tert.butylester is added to a mixture of 5.44 g (21.55 mmol) of 4,4-diphenyl-cyclohexanol and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichloromethane/acetone= 20:10:1).

Yield: 6.16 g (78% of theory) of a colorless, viscous oil Elementary analysis: Cld: C 78.65 H 8.25; Fnd: C 78.48 H 8.41;

b) 3-(4,4-Diphenylcyclohexyl)-3-oxapropionic acid 6 g (16.37 mmol) of the title compound of Example 33a is dissolved in 100 ml of trifluoroacetic acid, and it is stirred for 6 hours at room temperature. It is evaporated to the dry state, and the residue is chromatographed on silica gel. (Mobile solvent: hexane/diethyl ether=5:1/+2% acetic acid)

Yield: 4.7 g (93% of theory) of a colorless solid Elementary analysis: Cld: C 77.39 H 7.14; Fnd: C 77.18 H 7.38;

c) 1,4,7-Tris{1,4,7-tris(N-t.butyloxycarbonylmethyl)-10-[N-(4,7-diaza-3,6,9-trioxo-nonane-2,9-diyl)]-1,4,7,10-tetraazacyclododecane}-10-<N-[3-(4,4-diphenylcyclohexyl)-3-oxapropionyl]>-1,4,7,10-tetraazacyclododecane 2.90 g (9.33 mmol) of the title compound of Example 33b and 10.37 g (4.67 mmol) of the title compound of Example 15c are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/methanol=25:1)

Yield: 10.84 g (93% of theory) of a colorless, viscous oil Analysis: Cld: C 61.08 H 8.64 N 12.35; Fnd: C 60.91 H 8.85 N 12.21;

d) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-<N-[3-(4,4-diphenylcyclohexyl)-3-oxapropinyl]>-1,4,7,10-tetraazacyclododecane 10.49 g (4.2 mmol) of the title compound of Example 33c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.86 g (95% of theory) of a colorless, amorphous solid Water content: 10.1%; Elementary analysis (relative to anhydrous substance): Cld: C 44.23 H 5.43 N 12.47 Gd 19.09; Fnd: C 44.08 H 5.65 N 12.28 Gd 18.91;

EXAMPLE 34 a) 3-(4-Nonanylphenyl)-3-oxapropionic acid-t.butylester 10.51 g (53.9 mmol) of bromoacetic acid-tert.butylester is added to a mixture of 4.75 g (21.55 mmol) of 4-(nonanyl)-phenol and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichloromethane/acetone= 20:10:1).

Yield: 6.7 g (93% of theory) of a colorless, viscous oil Elementary analysis: Cld: C 75.41 H 10.24; Fnd: C 75.28 H 10.39;

b) 3-(4-Nonanylphenyl)-3-oxapropionic acid 6.6 g (19.73 mmol) of the title compound of Example 34a is dissolved in 100 ml of trifluoroacetic acid, and it is stirred for 6 hours at room temperature. It is evaporated to the dry state, and the residue is chromatographed on silica gel. (Mobile solvent: hexane/diethyl ether=5:1/+2% acetic acid)

Yield: 5.16 g (94% of theory) of a colorless solid Elementary analysis: Cld: C 73.35 H 10.24; Fnd: C 73.21 H 10.41;

c) 1,4,7-Tris{1,4,7-tris{N-t.butyloxycarbonylmethyl)-10-[N-(4,7-diaza-3,6,9-trioxo-nonane-2,9-diyl)]-1,4,7,10-tetraazacyclododecane}-10-<N-[3-(4-nonanylphenyl)-3-oxapropionyl]>-1,4,7,10-tetraazacyclododecane 2.59 g (9.33 mmol) of the title compound of Example 34b and 10.37 g (4.67 mmol) of the title compound of Example 8a are dissolved in 100 ml of dimethylformamide, and 3.71 g (15 mmol) of 2-ethoxy-1-ethoxycarbonyl-1,2-dihydroquinoline is added at 0° C. It is stirred for 24 hours at room temperature. It is evaporated to the dry state in a vacuum, and the residue is chromatographed on silica gel (mobile solvent: methylene chloride/2-propanol=25:1)

Yield: 10.34 g (93% of theory) of a colorless, viscous oil Elementary analysis: Cld: C 61.42 H 9.15 N 8.28; Fnd: C 61.27 H 9.30 N 8.05;

d) 1,4,7-Tris{1,4,7-tris(N-carboxylatomethyl)-10-[N-(4,7-diaza-3,6,9-trioxo-nonane-2,9-diyl)]-1,4,7,10-tetraazacyclododecane, Gd complex}-10-<N-[3-(4-nonanylphenyl)-3-oxapropionyl]>-1,4,7,10-tetraazacyclododecane 10 g (4.2 mmol) of the title compound of Example 34c is dissolved in 200 ml of trifluoroacetic acid, and it is stirred for 12 hours at room temperature. It is evaporated to the dry state. The residue is dissolved in 100 ml of water and set at pH 3.3 with 5% aqueous sodium hydroxide solution. Then, 2.28 g (6.3 mmol) of gadolinium oxide is added, and it is stirred for 3 hours at 90° C. It is allowed to reach room temperature, set at pH 7.0 with 5% aqueous sodium hydroxide solution, and the solution is dialyzed in an ultrafiltration cell (Amicon® YM-1), 6 passes. The contents of the ultrafiltration cell are freeze-dried.

Yield: 9.93 g (97% of theroy) of a colorless, amorphous solid water content: 11.0% Elementary analysis (relative to anhydrous substance): Cld: C 43.34 H 5.66 N 12.63 Gd 19.34; Fnd: C 43.18 H 5.81 N 12.47 Gd 19.15;

EXAMPLE 35

MRI Experiments on Animals with Induced Renal Infarctions

Enhancement in the MRI experiment was studied after one-time intravenous administration of the substance from Example 1d in animals with experimentally induced renal necroses or infarctions.

The induction of the renal infarctions was carried out on anesthetized (Rompun®/Ketavet®, i.p.) rats (Han. Wistar, Schering SPF, about 200 g of body weight) by occlusion of a (caudal) branch of the left renal artery. The contrast medium was administered (dose: 100 μmol of Gd/kg of body weight) about 24 hours after the induction of infarction. The animals were studied before and up to 24 hours after contrast medium administration by MR-tomography (SISCO SIS 85, 2 tesla; SE sequence, $T_R$: 400 ms, $T_E$: 15 ms, nt=4, ni=128, FOV: 12*7 cm, SD≈3 mm, 1 layer each axial or coronary).

After the MRI experiments were completed, the anesthetized animals were sacrificed by exsanguination (via the V. cava), and both kidneys were prepared. To verify the infarction (size and position), the left (infarcted) kidney was removed and sliced into disks, and then NBT ("vital") coloring was carried out.

Figure 1B:
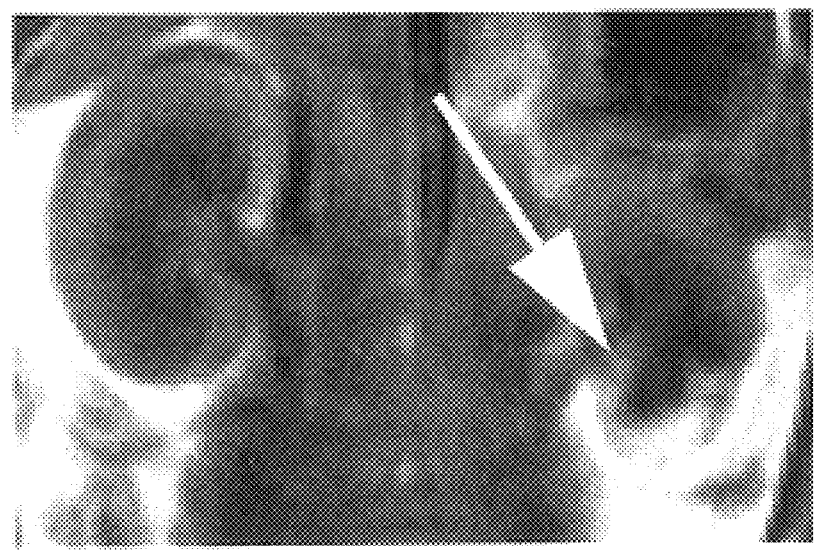

Immediately after substance administration, the nonperfused portion of the kidneys in each case was shown as a hypointense area (see FIG. 1, Part a). Starting at about 15–30 minutes p.i., however, the signal intensity increased somewhat in the non-perfused area or the size of the delimited (low-signal) area decreased (slow diffusion in the necrosis). In the late phase (24 hours p.i.), a considerable enhancement in the necrotic area of the kidneys was noted in all of the animals studied (see FIG. 1, Part b). The delineation of the necrotic area in the MRI experiment correlated very well with the results of the histological "vital" coloring.

EXAMPLE 36

MRI Experiments on Animals with Ethanol-Induced Necrosis

Enhancement after one-time administration of the substance from Example Id was studied in the MRI experiment in animals with experimentally induced liver necroses.

The induction of the necroses was carried out on rats (Han. Wistar, Schering SPF, about 200 g of body weight) by percutaneous administration of 200 μl of ethanol (80%) in the liver. The contrast medium was administered (dose: 100 μmol of Gd/kg of body weight) about 24 hours after the induction of necrosis. The animals were studied before and up to 24 hours after contrast medium administration by MR-tomography (SISCO SIS 85, 2 tesla; SE sequence, $T_R$: 400 ms, $T_E$: 15 ms, nt=4, ni=128, FOV: 7*7 cm, SD≈3 mm, 1 layer each axial).

After the MRI experiments were completed, the anesthetized animals were sacrificed by exsanguination (via the V. cava), the liver was prepared, and to evaluate the liver necrosis (with respect to size and position), NBT ("vital") coloring was carried out.

Figure 2A:
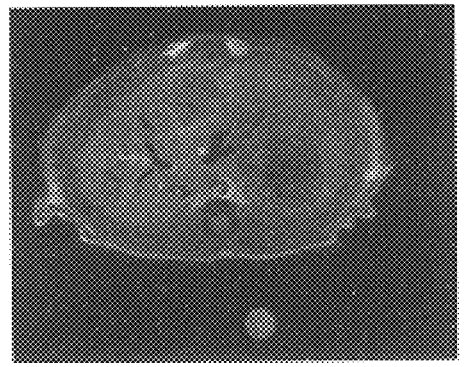
Figure 2B:
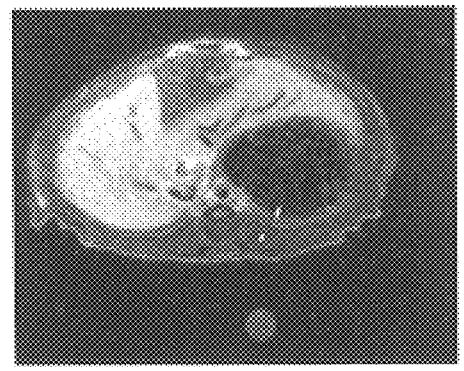
Figure 2C:
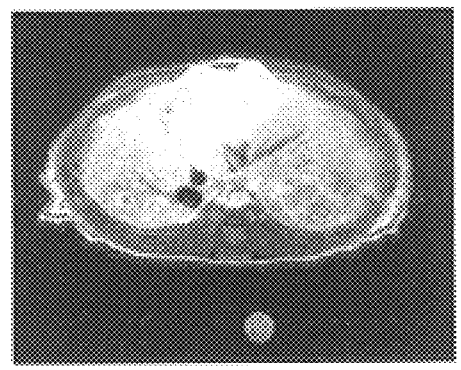

Immediately after substance administration, the necrotic portion of the liver in each case was shown as a poorly distinguished, weakly hypointense area (see FIG. 2, Part b). In the late phase (24 hours p.i.), however, a considerable enhancement in the necrotic area of the liver was noted in all of the animals studied (see FIG. 2, Part c). The delineation of the necrotic area in the MRI experiment correlated very well with the results of the histological "vital" coloring.

EXAMPLE 37

MRI Experiments on Animals with Induced Myocardial Infarction

Enhancement in the MRI experiment was studied after one-time intravenous administration of the substance from Example 18b in animals with experimentally induced myocardial infarction.

The induction of the myocardial infarctions was carried out on anesthetized (Rompun®/Ketavet®, i.p.) rats (Han. Wistar, Schering SPF, about 200 g of body weight) by occlusion of the left coronary artery. The contrast medium was administered (dose: 200 μmol of Gd/kg of body weight) about 24 hours after the induction of infarction. The animals were studied before and up to 24 hours after contrast medium administration by MR-tomography (SISCO SIS 85, 2 tesla; SE sequence, $T_R$: 400 ms, $T_E$: 15 ms, nt=4, ni=128, FOV: 12*7 cm, SD≈3 mm, 1 layer each axial or coronary).

After the MRI experiments were completed, the anesthetized animals were sacrificed by exsanguination (via the V. cava), and the heart was prepared. To verify the infarction (size and position), the heart was removed and sliced into disks, and then NBT ("vital") coloring was carried out.

Figure 3A:
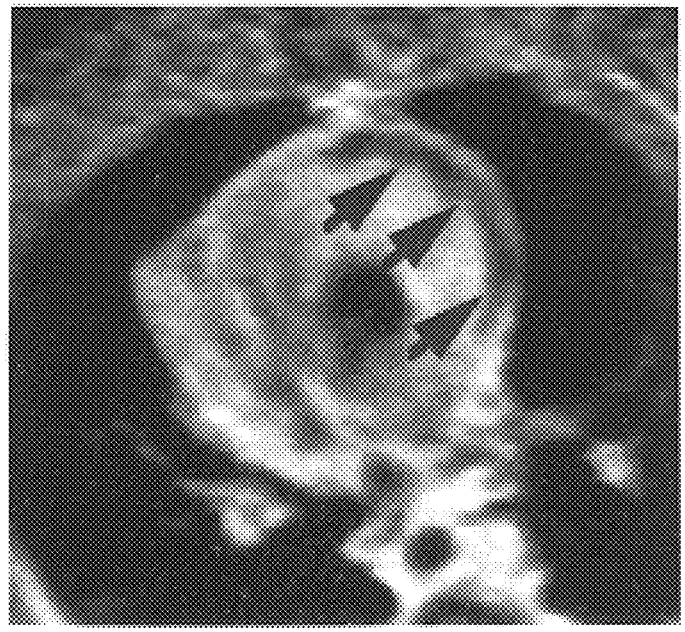
Figure 3B:
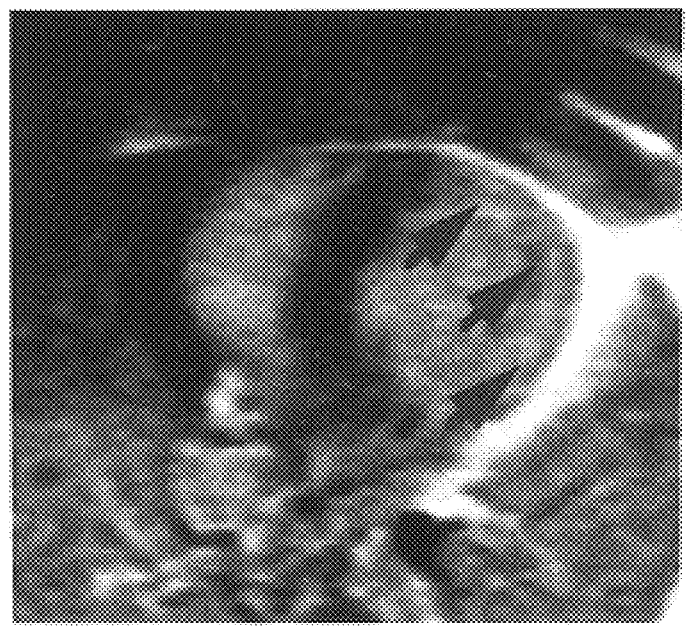

Immediately after substance administration, the nonperfused portion of the myocardium in each case was shown as a hypointense area (see FIG. 3, Part a). Starting at about 30 minutes p.i., however, the signal intensity increased somewhat in the non-perfused area or the size of the delimited (low-signal) area decreased (slow diffusion in the necrosis). In the late phase (24 hours p.i.), a considerable enhancement in the necrotic area of the myocardium was noted (see FIG. 3, Part b). The delineation of the myocardium was noted (see FIG. 3, Part b). The delineation of the necrotic area in the mri experiment correlated very well with the results of the histological "vital" coloring.

What is claimed is:

1. Compounds of general formula I

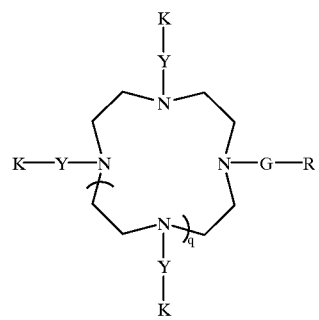

in which q means a number 1, 2 or 3,

G is a direct bond, an $SO_2$ or a CO group,

K stands for a metal complex or its salts of organic and/or inorganic bases or amino acids or amino acid amides, R is an unbranched or branched $C_4$–$C_{30}$ hydrocarbon chain, which optionally is substituted by 1–2 amino groups, 1–2 $SO_2$ groups, 1–5 OH groups, 1–5 $OR^1$ groups with $R^1$ meaning a $C_1$–$C_6$ alkyl group, 1 NH-K group, 1–3 carboxy groups, 1–2 aliphatic or 1–3 aromatic rings, and which optionally contains 1–6 amide groups, 1–2 sulfur atoms, 1–6 oxygen atoms, 1–2 aliphatic or 1–3 aromatic rings, whereby the aromatic rings are optionally substituted with 1–2 chlorine atoms, 1–2 acid groups, 1–2 $OR^1$ groups or 1–2 $C_1$–$C_6$ alkyl groups, Y is a direct bond or a chain of general formula II or III:

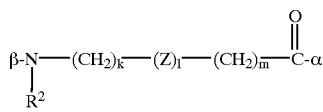   (II)

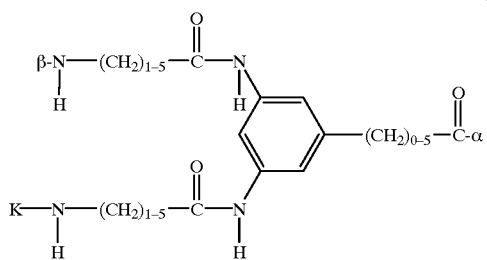   (III)

in which $R^2$ is a hydrogen atom, a phenyl group, a benzyl group or a $C_1$–$C_7$ alkyl group, which optionally is substituted with a carboxy group, a methoxy group or a hydroxy group, Z is a polyglycol ether group with up to 5 glycol units or a molecule portion of general formula IV

   (IV), in which $R^3$ is a $C_1$–$C_{10}$ alkyl radical, a carboxylic acid with 1–7 carbon atoms, a phenyl group, a benzyl group or a —$(CH_2)_{1-5}$—NH—K group, represents the bond to the nitrogen atom of the skeleton chain, β represents the bond to metal complex K, and in which variables k and m stand for natural numbers between 0 and 10 and l stands for 0 or 1.

2. Compounds according to claim 1, characterized in that K represents a complex of general formula V, VI, VII or VIII,

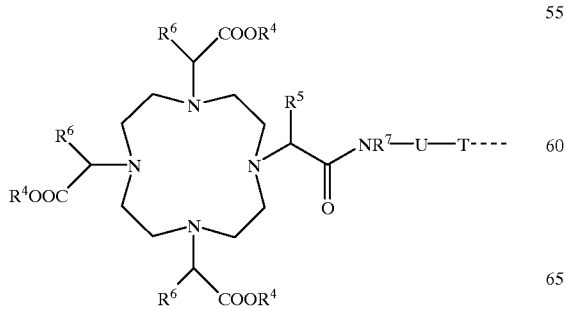   (V)

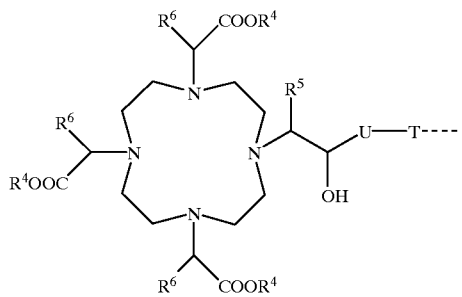   (VI)

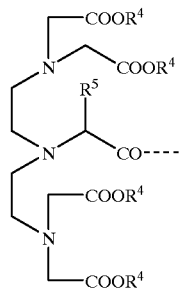   (VII)

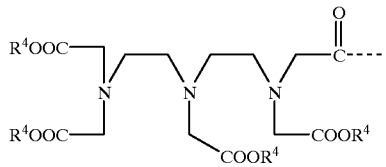   (VIII)

whereby $R^4$, independently of one another, are a hydrogen atom or a metal ion equivalent of the elements of atomic numbers 20–32, 37–39, 42–44, 49 or 57–83, provided that at least two of substituents $R^4$ stand for a metal ion equivalent of the above-mentioned elements, $R^5$ is a hydrogen atom or a straight-chain, branched, saturated or unsaturated $C_1$–$C_{30}$ hydrocarbon chain, which optionally is substituted by 1–5 hydroxy, 1–3 carboxy or 1 phenyl group(s) and/or optionally is interrupted by 1–10 oxygen atoms, 1 phenylene or 1 phenylenoxy group, $R^6$ is a hydrogen atom, a straight-chain or branched $C_1$–$C_7$ alkyl radical, a phenyl or benzyl radical, $R^7$ is a hydrogen atom, a methyl or ethyl group, which optionally is substituted by a hydroxy or carboxy group, U is a straight-chain, branched, saturated or unsaturated $C_1$–$C_{20}$ hydrocarbon chain that optionally contains 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups, 1–10 oxygen, 1–5 sulfur and/or 1–5 nitrogen atoms and/or optionally is substituted by 1–5 hydroxy, 1–2 mercapto, 1–5 oxo, 1–5 thioxo, 1–3 carboxy, 1–5 carboxyalkyl, 1–5 ester and/or 1–3 amino groups, whereby the optionally contained phenylene groups can be substituted by 1–2 carboxy, 1–2 sulfone or 1–2 hydroxy groups, T stands for a —CO—β, —NHCO—β or —NHCS—β group, whereby β indicates the binding site to Y.

3. Compounds according to claim 1, wherein R is a group of general formula IX,

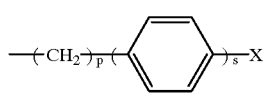
(IX)

in which p stands for numbers 0 to 25 and s stands for 0, 1 or 2, and p and s are not zero at the same time, and in which X is a hydrogen atom, a methyl group, a carboxyl group, an OH group, an $OCH_3$ group, a $CONH_2$ group, a chlorine atom, a $C_1$–$C_{10}$ alkyl chain, an O—$C_nH_{2n+1}$ group, an O—$(CH_2)_n$—COOH group, an —O—$(CH_2CH_2)_r$—$C_nH_{2n+1}$ group or an NH—CO—$C_nH_{2n+1}$ group, with n=1–15 and r=1–5.

4. Compounds according to claim 1, wherein R is one of the following groups:

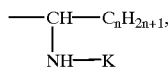

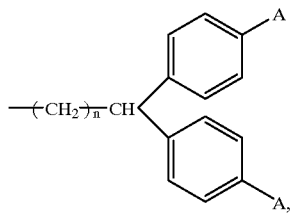

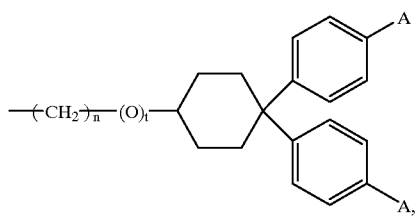

in which n=1–15, t=0 or 1, and A means a hydrogen atom, a chlorine atom or an $OCH_3$ group.

5. Compounds according to claim 1, wherein G and R together have one of the following structures:
—CO—$C_{15}H_{31}$, —CO—$C_{14}H_{29}$, —CO—$C_{13}H_{27}$, —CO—$C_{10}H_{20}$—NH—CO—$C_6H_{13}$, —CO—$C_6H_{13}$, —CO—$CH_2$—O—$CH_2$$CH_2$—O—$C_{10}H_{21}$, —CO—$CH_2$—O—$C_{13}H_{27}$, —$C_{15}H_{31}$, —$C_{14}H_{29}$, —$SO_2$—$C_{13}H_{27}$, —$SO_2$—$C_{14}H_{29}$, —$SO_2$—$C_{15}H_{31}$,

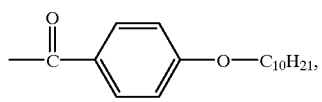

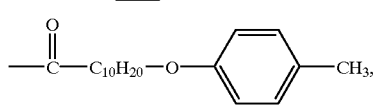

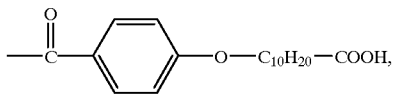

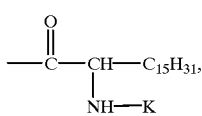

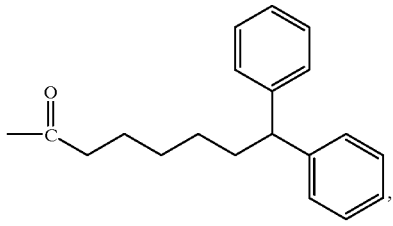

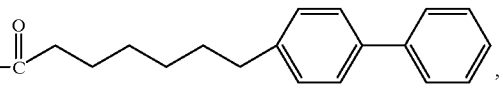

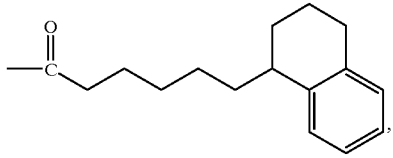

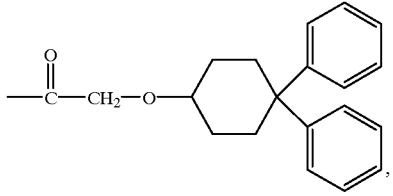

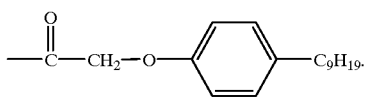

6. Compounds according to claim 1, wherein Y is a molecule portion with one of the following structures:

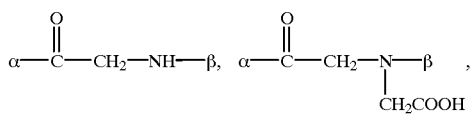

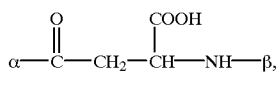

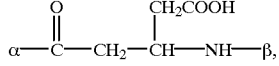

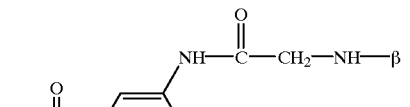

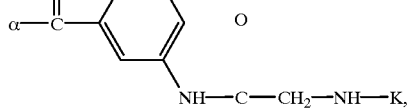

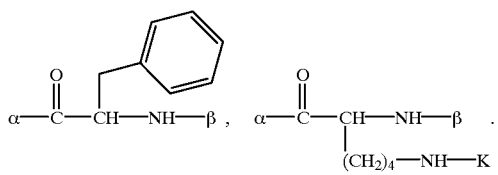

7. Compounds according to claim 2,
wherein
the $C_1$–$C_{20}$ alkylene chain that stands for U contains the groups:
—$CH_2NHCO$—, —$NHCOCH_2O$—, —$NHCOCH_2OC_6H_4$—, —$N(CH_2CO_2H)$—, —$CH_2OCH_2$—, —$NHCOCH_2C_6H_4$—, —$NHCSNHC_6H_4$—, —$CH_2OC_6H_4$—, —$CH_2CH_2O$—
and/or is substituted by groups —COOH and —$CH_2COOH$.

8. Compounds according to claim 2,
wherein
U stands for a
—$CH_2$—, —$CH_2CH_2$—, —$CH_2CH_2CH_2$—, —$C_6H_4$—, —$C_6H_{10}$—, —$CH_2C_6H_4$—, —$CH_2NHCOCH_2CH(CH_2CO_2H)$—$C_6H_4$—, —$CH_2NHCOCH_2OCH_2$—, —$CH_2NHCOCH_2C_6H_4$ group.

9. Compounds according to claim 1,
wherein
K has one of the following structures:

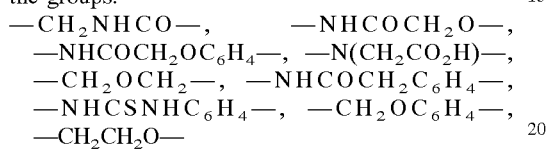

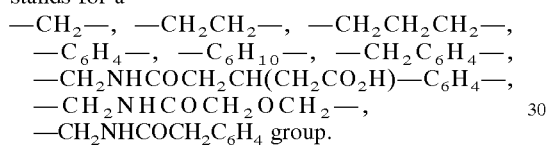

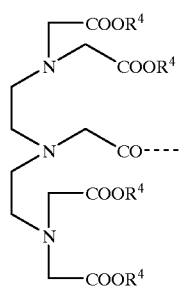

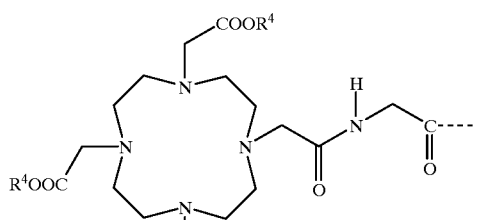

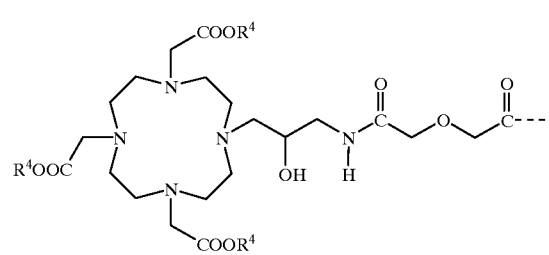

in which $R^4$ has the meaning that is defined in claim 2.

10. Compounds according to claim 1,
wherein
q stands for number 1.

11. Process for the production of the compounds of general formula I,
wherein compounds of general formula I'

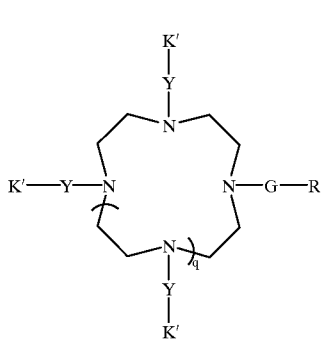

(I')

in which K' stands for K, with $R^4$ meaning a hydrogen atom or a carboxy protective group,
are reacted, after the optionally present protective groups are cleaved off, in a way known in the art, with at least one metal oxide or metal salt of an element of atomic numbers 20–32, 37–39, 42–44, 49 or 57–83 and optionally then still present acid hydrogen atoms are substituted completely or partially by cations of inorganic and/or organic bases, amino acids or amino acid amides in the complex compounds that are thus obtained.

12. Process for the production of compounds of general formula I, wherein a compound of general formula I″

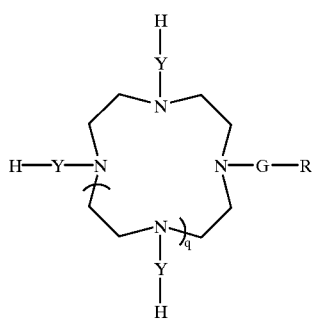
(I″)

is reacted with a complex V' or VI',

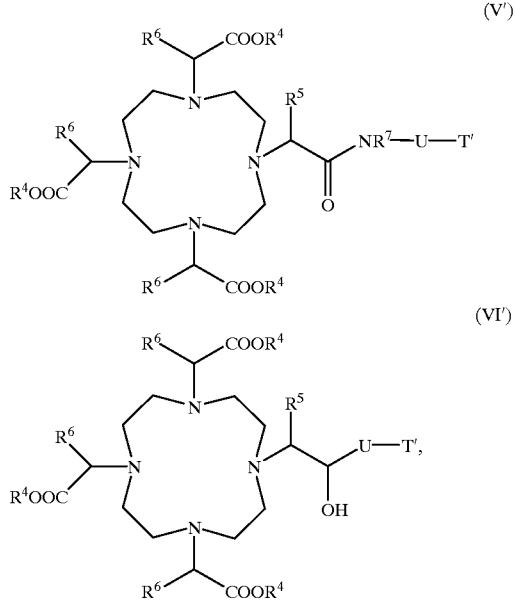

whereby T' stands for a —C*O, —COOH, —N=C=O or —N=C=S group and —C*O stands for an activated carboxyl group, and radicals $R^4$ and $R^7$ are defined as in claim 2, provided that at least two (in the case of divalent metals) or three (in the case of trivalent metals) of substituents $R^4$ stand for a metal ion equivalent of the above-mentioned elements and provided that optionally other carboxyl groups are present in the form of their salts with inorganic and/or organic bases, amino acids or amino acid amides.

13. Pharmaceutical agents that contain at least one physiologically compatible compound according to claim 1, optionally with the additives that are commonly used in galenicals.

14. Process for the production of pharmaceutical agents according to claim 13,
   wherein the compounds that are present in water or physiological salt solution, optionally with the additives that are commonly used in galenicals, are brought into a form that is suitable for enteral or parenteral administration.

15. A method of $^1$H-NMR diagnosis or $^1$H-NMR spectroscopy, comprising administering to a patient at least one physiologically compatible compound according to claim 1, optionally comprising an additive which is commonly used in galenicals, as a contrast agent.

16. A method of diagnostic radiology, comprising administering to a patient at least one physiologically compatible compound according to claim 1, optionally comprising an additive which is commonly used in galenicals, as a contrast agent.

17. A method of radiodiagnosis or radiotherapy, comprising administering to a patient at least one physiologically compatible compound according to claim 1, optionally comprising an additive which is commonly used in galenicals.

18. A method according to claim 15, for localization of an infarction or a necrosis.

19. A method according to claim 16, for localization of an infarction or a necrosis.

* * * * *